(12) United States Patent
Dwyer et al.

(10) Patent No.: US 7,022,141 B2
(45) Date of Patent: Apr. 4, 2006

(54) ALIGNMENT DEVICE FOR MODULAR IMPLANTS AND METHOD

(75) Inventors: Kimberly A. Dwyer, Fort Wayne, IN (US); David Daniels, War saw, IN (US); Brad Parker, War saw, IN (US)

(73) Assignee: Depuy Products, Inc., Warsaw, IN (US)

(*) Notice: Subject to any disclaimer, the term of this patent is extended or adjusted under 35 U.S.C. 154(b) by 123 days.

(21) Appl. No.: 10/327,196

(22) Filed: Dec. 20, 2002

(65) Prior Publication Data

US 2004/0122437 A1 Jun. 24, 2004

(51) Int. Cl.
*A61F 2/32* (2006.01)
(52) U.S. Cl. .................................. 623/22.12
(58) Field of Classification Search ............. 623/22.12, 623/22.11; 606/99, 104, 96, 98, 79–80, 53
See application file for complete search history.

(56) References Cited

U.S. PATENT DOCUMENTS

| | | | |
|---|---|---|---|
| 2,492,249 A | 12/1949 | Willard et al. | |
| 3,271,868 A | 9/1966 | Kuntscher et al | |
| 3,801,989 A * | 4/1974 | McKee .................... | 623/22.12 |
| 3,810,312 A | 5/1974 | Carson | |
| 4,131,998 A | 1/1979 | Spears | |
| 4,608,055 A | 8/1986 | Morrey et al. | |
| 4,658,808 A | 4/1987 | Link | |
| 4,716,894 A | 1/1988 | Lazzeri et al. | |
| 4,917,530 A | 4/1990 | Engelhardt et al. | |
| 4,969,911 A | 11/1990 | Greene | |
| 5,002,581 A | 3/1991 | Paxson et al. | |
| 5,064,427 A * | 11/1991 | Burkinshaw ................. | 606/99 |
| 5,100,407 A | 3/1992 | Conrad et al. | |
| 5,133,760 A | 7/1992 | Petersen et al. | |
| 5,135,529 A | 8/1992 | Paxson et al. | |
| 5,197,989 A | 3/1993 | Hinckfuss et al. | |
| 5,201,882 A | 4/1993 | Paxson | |
| 5,370,706 A | 12/1994 | Bolesky et al. | |
| 5,476,466 A * | 12/1995 | Barrette et al. ............... | 606/86 |
| 5,507,824 A | 4/1996 | Lennox | |
| 5,507,830 A | 4/1996 | DeMane et al. | |
| 5,514,136 A * | 5/1996 | Richelsoph ................... | 606/99 |
| 5,601,567 A | 2/1997 | Swajger et al. | |
| 5,607,431 A | 3/1997 | Dudasik et al. | |
| 5,645,607 A | 7/1997 | Hickey | |
| 5,658,349 A | 8/1997 | Brooks et al. | |
| 5,674,225 A * | 10/1997 | Muller ......................... | 606/99 |

(Continued)

FOREIGN PATENT DOCUMENTS

EP 0381893 A1 8/1990

(Continued)

OTHER PUBLICATIONS

European Search Report for Eurpoean Application No. 03257810.6-2310, dated Apr. 5, 2004, 2 pages.

(Continued)

*Primary Examiner*—Alvin J. Stewart

(57) ABSTRACT

An instrument (200) for at least one of replicating and measuring the angular orientation of a first component (54) of a prosthesis (51) to a second component (52) of the prosthesis (51) for use in joint arthroplasty. The instrument (200) includes a first member (202) for cooperation with the first component (54), a second member (210) for cooperation with the second component (52), and a feature (220). The feature (220) cooperates with the first member (202) and the second member (210) for at least one of replicating and measuring the relative angular orientation of the first component (54) with respect to the second component (52).

18 Claims, 30 Drawing Sheets

U.S. PATENT DOCUMENTS

| | | | |
|---|---|---|---|
| 5,728,128 A | | 3/1998 | Crickenberger et al. |
| 5,766,261 A | | 6/1998 | Neal et al. |
| 5,776,200 A | | 7/1998 | Johnson et al. |
| 5,792,143 A | | 8/1998 | Samuelson et al. |
| 5,810,829 A | | 9/1998 | Elliott et al. |
| 5,810,830 A | | 9/1998 | Noble et al. |
| 5,824,068 A | * | 10/1998 | Bugge ........................ 623/2.11 |
| 5,849,015 A | * | 12/1998 | Haywood et al. .............. 606/99 |
| 5,858,020 A | | 1/1999 | Johnson et al. |
| 5,860,969 A | | 1/1999 | White et al. |
| 5,876,459 A | | 3/1999 | Powell |
| 5,879,391 A | | 3/1999 | Slamin |
| 5,885,299 A | * | 3/1999 | Winslow et al. .............. 606/99 |
| 5,888,245 A | * | 3/1999 | Meulink et al. .......... 623/23.35 |
| 5,902,339 A | * | 5/1999 | Keller ..................... 623/20.31 |
| 5,906,644 A | | 5/1999 | Powell |
| 5,919,195 A | | 7/1999 | Wilson et al. |
| 5,935,172 A | | 8/1999 | Ochoa et al. |
| 5,951,564 A | * | 9/1999 | Schroder et al. ............ 606/100 |
| 5,951,606 A | | 9/1999 | Burke |
| 5,976,147 A | | 11/1999 | LaSalle et al. |
| 5,976,188 A | | 11/1999 | Dextradeur et al. |
| 5,989,259 A | * | 11/1999 | Penenberg et al. ............ 606/99 |
| 5,993,455 A | | 11/1999 | Noble |
| 6,027,507 A | | 2/2000 | Anderson et al. |
| 6,045,556 A | | 4/2000 | Cohen |
| 6,071,311 A | | 6/2000 | O'Neil et al. |
| 6,080,162 A | | 6/2000 | Dye et al. |
| 6,102,950 A | | 8/2000 | Vaccaro |
| 6,102,956 A | | 8/2000 | Kranz |
| 6,110,179 A | * | 8/2000 | Flivik et al. ................... 606/99 |
| 6,113,605 A | * | 9/2000 | Storer ........................ 606/99 |
| 6,117,138 A | | 9/2000 | Burrows et al. |
| 6,126,694 A | | 10/2000 | Gray, Jr. |
| 6,165,177 A | * | 12/2000 | Wilson et al. .............. 606/100 |
| 6,179,877 B1 | | 1/2001 | Burke |
| 6,193,759 B1 | | 2/2001 | Ro et al. |
| 6,197,065 B1 | | 3/2001 | Martin et al. |
| 6,206,844 B1 | | 3/2001 | Reichel et al. |
| 6,224,605 B1 | | 5/2001 | Anderson et al. |
| 6,238,435 B1 | | 5/2001 | Meulink et al. |
| 6,258,095 B1 | | 7/2001 | Lombardo et al. |
| 6,258,097 B1 | | 7/2001 | Cook et al. |
| 6,277,123 B1 | * | 8/2001 | Maroney et al. ............ 606/102 |
| 6,319,286 B1 | | 11/2001 | Fernandez et al. |
| 6,330,845 B1 | | 12/2001 | Meulink |
| 6,332,886 B1 | | 12/2001 | Green et al. |
| 6,355,068 B1 | | 3/2002 | Doubler et al. |
| 6,361,563 B1 | | 3/2002 | Terrill-Grisoni et al. |
| 6,432,110 B1 | | 8/2002 | Richelsoph |
| 2001/0001121 A1 | | 5/2001 | Lombardo et al. |
| 2001/0007957 A1 | | 7/2001 | Martin et al. |
| 2001/0053935 A1 | | 12/2001 | Hartdegen et al. |

FOREIGN PATENT DOCUMENTS

| | | |
|---|---|---|
| EP | 0381893 B1 | 6/1994 |
| EP | 0 824 013 A1 | 2/1998 |
| EP | 1 004 283 A2 | 5/2000 |
| EP | 1 004 283 A3 | 5/2000 |
| EP | 1022001 A | 7/2000 |
| EP | 1004283 A3 | 3/2002 |
| EP | 1234558 A2 | 8/2002 |
| EP | 1234558 A3 | 9/2002 |
| FR | 2416002 | 8/1979 |
| FR | 2492249 | 4/1982 |
| FR | 2684287 A1 | 4/1993 |
| FR | 2 705 558 A1 | 12/1994 |
| WO | WO 96/15739 | 5/1996 |
| WO | WO 0217826 A | 3/2002 |

OTHER PUBLICATIONS

European Search Report for Eurpoean Application No. 03257813.0-2310, dated May 11, 2004, 2 pages.

European Search Report for Eurpoean Application No. 03257816.3-2210, dated May 18, 2004, 2 pages.

* cited by examiner

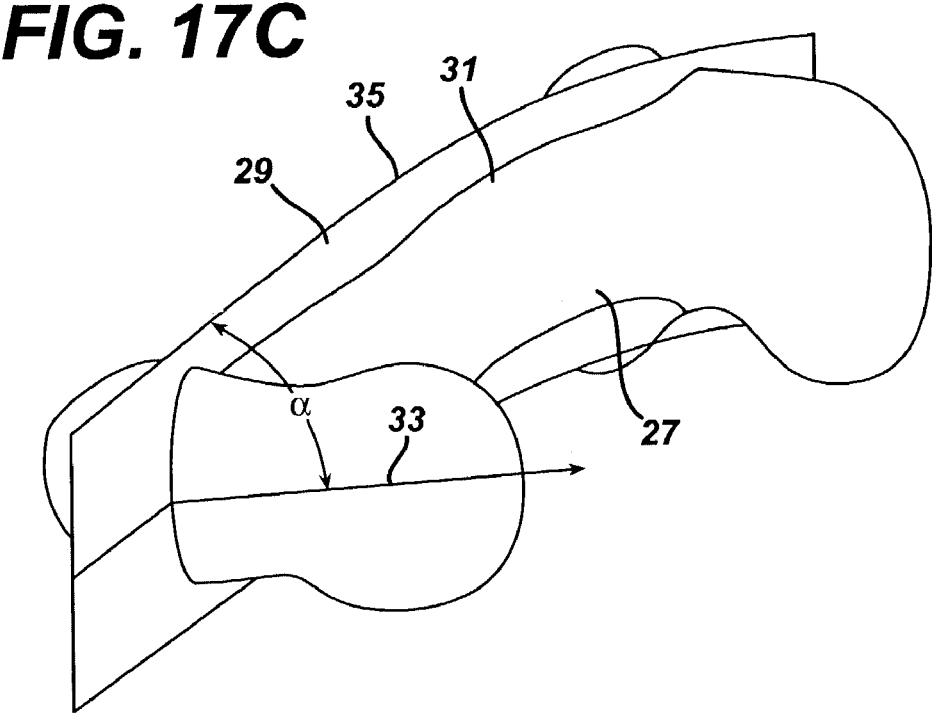
FIG. 17C
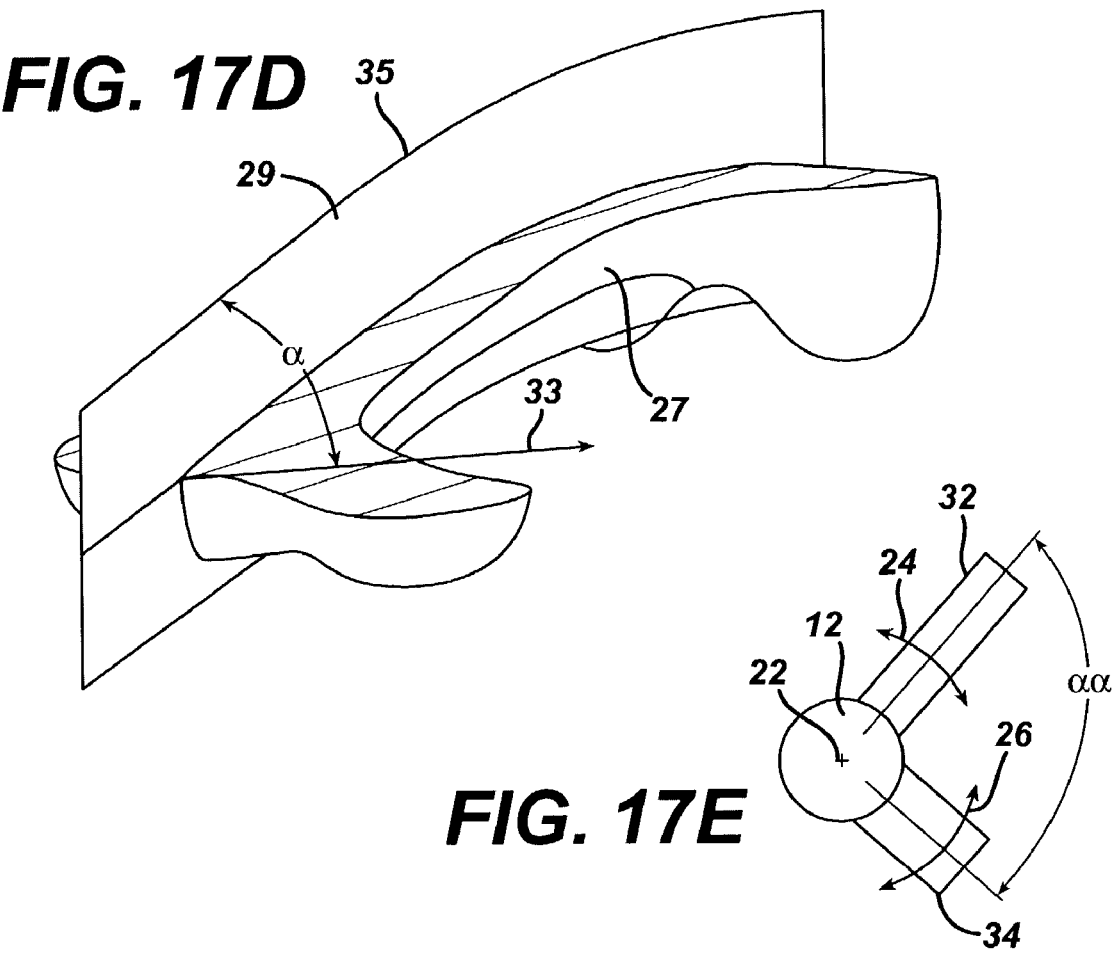
FIG. 17D
FIG. 17E

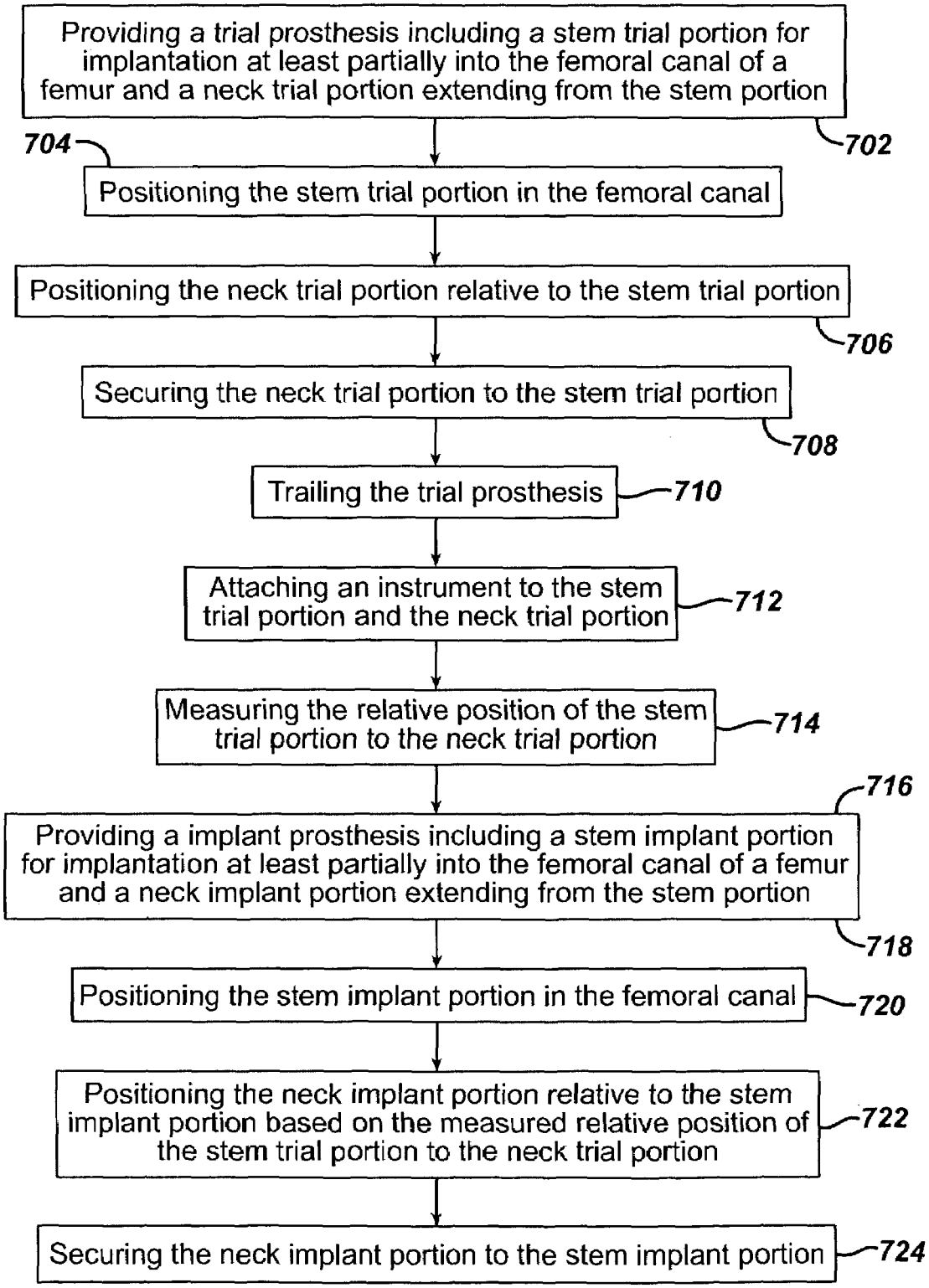

ALIGNMENT DEVICE FOR MODULAR IMPLANTS AND METHOD

CROSS-REFERENCE TO RELATED APPLICATIONS

Cross reference is made to the following applications: DEP 644 entitled "ADJUSTABLE BIOMECHANICAL TEMPLATING & RESECTION INSTRUMENT AND ASSOCIATED METHOD", DEP 725 entitled "INSTRUMENT AND ASSOCIATED METHOD OF TRIALING FOR MODULAR HIP STEMS" and DEP 5004 entitled "MODULAR HIP STEMS AND ASSOCIATED METHOD OF TRIALING" filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be possible otherwise to do so. Artificial joints usually comprise metal, ceramic and/or plastic components that are fixed to existing bone.

Such joint replacement surgery is otherwise known as "joint arthroplasty". Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

Many designs and methods for manufacturing implantable articles, such as bone prostheses are known to exist. Such bone prostheses include components of artificial joints, such as elbows, hips, knees and shoulders.

Currently, in total hip arthroplasty, a major critical concern is the instability of the joint. Instability is associated with dislocation. Dislocation is particularly a problem in total hip arthroplasty.

Factors related to dislocation include surgical technique, implant design, implant positioning and patient related factors. In total hip arthroplasty, implant systems address this concern by offering a series of products with a range of lateral offsets, neck lengths, head lengths and leg lengths. The combination of these four factors affects the laxity of the soft tissue. By optimizing the biomechanics, the surgeon can provide a patient a stable hip much more resistant to dislocation. In order to accommodate the range of patient and anthropometrics, a wide range of hip implant geometries are currently manufactured by DePuy Orthopaedics, Inc., the assignee of the current application and by other companies. In particular, the S-ROM® total hip systems offered by DePuy Orthopaedics, Inc. include three offsets, three neck lengths, four head lengths and one leg length adjustment. The combination of all these biomechanic options is rather complex.

Anteversion of a hip stem is closely linked to the stability of the joint. Improper version can lead to dislocation and patient dissatisfaction. Version control is important in all hip stems. However, it becomes a more challenging issue with the advent of stems with additional modularity.

The prior art has provided for some addressing of the anteversion problem. For example, the current S-ROM® stems have laser marking on the medial stem and the proximal sleeve. This marking enables the surgeon to measure relative alignment between these components. Since the sleeve has infinite anteversion, it is not necessarily oriented relative to a bony landmark that can be used to define anteversion. In fact, the sleeves are sometimes oriented with the spout pointing directly laterally into the remaining available bone.

Prior art stems may be aligned relative to patient's bony landmarks. These stems are monolithic stems. They cannot locate the neck independently of the distal stem. Therefore, the anteversion is limited. Most bowed, monolithic stems are sold in fixed anteversion. For example, at an anteversion of 15°, these monolithic stems have limited flexibility for rotational alignment since the distal stem must follow the bow of the patient's femur and this may not provide an optimal biomechanical result. Thus, a need for an instrument as well as implants that provide for anteversion alignment relative to a patient's bony landmark exists.

SUMMARY OF THE INVENTION

The present invention provides for an instrument and an associated method for allowing the surgeon to measure and orient anteversion of a modular hip stem either as a trial or an implant. The device works by mating with specific features on the distal stem component and the proximal body component of either an implant or a trial. The anteversion can thus be measured on trial components or actual implant components. Further, it can mate with the provisional trial components or the final implants when they are in the bone. The instrument can store the anteversion measured on the trial components and map that angular relationship to final implant components. Likewise, the instrument can be used to measure the anteversion on the final implant components.

For example, implants for use with the alignment device of the present invention may include two features. For example, the first of these features is a keyed geometry on the proximal aspect of the distal stem. The other primary feature on the implant may be in the form of keyed geometry on the proximal body of the implant. For example, the proximal body geometry may include holes in the proximal body, flats on the neck, or the outer faces of the neck itself.

The instrument may include features that correspond to the features on the implants. For example, the instrument may include a feature to mate with the keyed geometry on the proximal aspect of the distal stem. Further, the instrument may include a device for mating with holes in the proximal body, the flats on the neck or the outer surface of the neck. Such a feature to mate with the neck may be in the form of a yoke. Such a feature to mate with the proximal body may be in the form of pins to engage with the holes. The keyed geometry on the stem may communicate the rotational position of the bow to the top of the trial stem or the implant stem. The corresponding key on the instrument mates with this key way.

Simultaneously, the yoke of the instrument mates with the anterior-posterior flats on the neck. Alternatively, the yoke may mate with the taper on the neck itself. Alternatively, pins of the instrument can mate with the holes in the proximal body. The angular position is locked into or stored in the instrument. This stored angular position can be replicated on the implant.

The instrument of the present invention is designed to work with stems having two or more components. The first component is a proximal body that contains the neck and the second component contains the distal stem. The distal stem may be bowed to accommodate the natural bow of the femur. When the parts are assembled, the angular orientation between the bow of the distal stem component and the neck define the assembly anteversion. The instrument of the present invention mates with features on either a trial component or a final implant. When the instrument is used to determine the angle between the features on the trial component, the instrument measures the anteversion between the trial distal stem and the trial neck. The instrument allows the user to reproduce this angular relationship on the actual implant components. The instrument can also be used to measure the rotational relationship of the implants. For example, the instrument can measure the relationship between the neck and the bow of the distal stem. Alternatively, the stem can be implanted and the proximal body can be assembled at a preset, fixed angle. An additional alternative is the possibility to use a distal stem implant with a proximal trial and set the anteversion on the patient and replicate this with the proximal implant without removing the distal stem implant. This instrument can be used to orient a modular implant.

According to one embodiment of the present invention, an instrument for at least one of replicating and measuring the relative angular orientation of a first component of a prosthesis to a second component of the prosthesis with respect for use in joint arthroplasty is provided. The instrument includes a first member for cooperation with the first component and a second member. The second member cooperates with the second component. The instrument also includes a feature cooperating with the first member and the second member for at least one of replicating and measuring the relative angular orientation of the first component with respect to the second component.

According to another embodiment of the present invention, an instrument for at least one of replicating and measuring the relative angular orientation of first component of a prosthesis with respect to a second component of a femoral stem assembly of a hip prosthesis for use in total hip arthroplasty is provided. The instrument includes a first member for cooperation with the first component and a second member. The second member cooperates with the second component. The instrument further includes a feature cooperating with the first member and the second member for at least one of replicating and measuring the relative position of the first component with respect to the second component.

According to yet another embodiment of the present invention, a kit for use in joint arthroplasty is provided. The kit includes a prosthesis for use in joint arthroplasty including a first component and a second component. The second component is operably connected to the first component. The kit also includes an instrument for at least one of replicating and measuring the relative angular orientation of the first component to the second component. The instrument has a first member for cooperation with the first component, a second member for cooperation with the second component and a feature cooperating with the first member and the second member for at least one of measuring and replicating the relative angular orientation of the first component with respect to the second component.

According to a further embodiment of the present invention, a method for providing hip arthroplasty is provided. The method includes the steps of providing a trial prosthesis including a stem trial portion for implantation at least partially into the femoral canal of a femur and a neck trial portion extending from the stem portion and the step of positioning the stem trial portion in the femoral canal. The method also includes the steps of positioning the neck trial portion relative to the stem trial portion and securing the neck trial portion to the stem trial portion. The method further includes the steps of trialing the trial prosthesis and attaching an instrument to the stem trial portion and the neck trial portion. The method further includes the steps of measuring the relative position of the stem trial portion to the neck trial portion and providing an implant prosthesis including a stem implant portion for implantation at least partially into the femoral canal of a femur and a neck implant portion extending from the stem portion. The method further includes the steps of positioning the stem implant portion in the femoral canal and positioning the neck implant portion relative to the stem implant portion based on the to the stem implant portion based on the measured relative position of the stem trial portion to the neck trial portion, and securing the neck implant portion to the stem implant portion.

The technical advantages of the present invention include the ability to provide an absolute alignment to a clinically relevant bony landmark. For example, according to one aspect of the present invention, the instrument cooperates with an implant that is bowed to fit the medullary canal of a long bone such as a femur. The anterior bow of the femoral intramedullary canal defines a plane from which the angle of the femoral neck can be measured. The instrument of the present invention positively orients the proximal body and neck in absolute alignment with the bowed distal stem. Thus, the present invention provides absolute alignment to a clinically relevant bony landmark.

Another technical advantage of the present invention includes the ability of the current invention to be used on the back table outside the body and in location in the patient's bone. For example, according to one aspect of the present invention, the angular orientation feature of the distal stem, as well as the angular orientation feature of the proximal body and neck, are both accessible and utilized with the instrument in a position accessible to the surgeon while the implant is in position in the bone. Thus, the present invention provides for use on the back table and in the bone.

Another technical advantage of the present invention includes the ability of the instrument of the present invention to be used on trial components and on implants. For example, according to one aspect of the present invention, the angular orientation feature for the bowed distal stem for both an implant and a trial is located proximally so that the instrument of the present invention can locate the angular orientation of the bowed distal stem on either a trial or an implant. Similarly, the proximal body and neck implant and the proximal body and neck trial are designed with angular orientation features that cooperate with the instrument of the present invention, which may be located proximally on the implant and trial. The surgeon can thus use a distal stem trial and proximal body trial to intraoperatively set anteversion and then replicate it in the modular implant. Similarly, the surgeon can use a distal stem implant and a proximal body trial to intraoperatively set anteversion and then replace the proximal body trial with a proximal body implant leaving the distal stem implant in the patient's femur. Thus, the present invention provides for use of the orientation device on both trial components and on implants.

Another technical advantage of the present invention includes the ability of the proposed instrument to control the rotational alignment of the distal stem independently of the neck of the component. For example, according to one aspect of the present invention, the alignment device includes a feature for cooperation with an orientation feature for a bowed distal stem as well as an orientation feature for a proximal body. Thus, the present invention provides for rotational alignment of a distal stem independent of the neck of the component.

Another technical advantage of the present invention includes the ability to use CT measurement data or a predetermined version angle predetermined by any other method determined by the physician and reproduce the predetermined version angle. For example, according to one aspect of the present invention, the instrument includes indication or marks on the instrument corresponding to various predetermined version angles. Thus, the present invention provides for orienting the implant or trial at a predetermined version angle.

In primary hip surgery, many of the bony landmarks are obscured by osteophyte formation, post-traumatic deformities, bone loss, etc. The one true landmark that is always present is the intramedullary canal. In a revision surgery, the anatomy is typically more severely affected and the standard referencing landmarks may no longer be available or are compromised. Hence, this instrument allows the surgeon to find, measure and optimize an anteversion relative to the anteriorly bowed intramedullary canal. This bowed canal is always present and is independent of excess tissue, poor x-ray techniques, proximal bone loss, patient positioning on the table, certain proximal deformities such as DDH, neck fractures, and so forth. In fact, it is one part of the anatomy that the surgeon almost always has available to use in extremely difficult cases.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 17C is a perspective view of a femur, taken from the proximal end, showing a plane through the anterior bow of the femur and the anatomic anteversion angle;

FIG. 17D is a cross-section of the femur of FIG. 17C;

FIG. 17E is a top view of the stem of FIG. 17;

FIG. 27 is a flow chart of a method of performing arthroplasty according to the present invention.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 16:
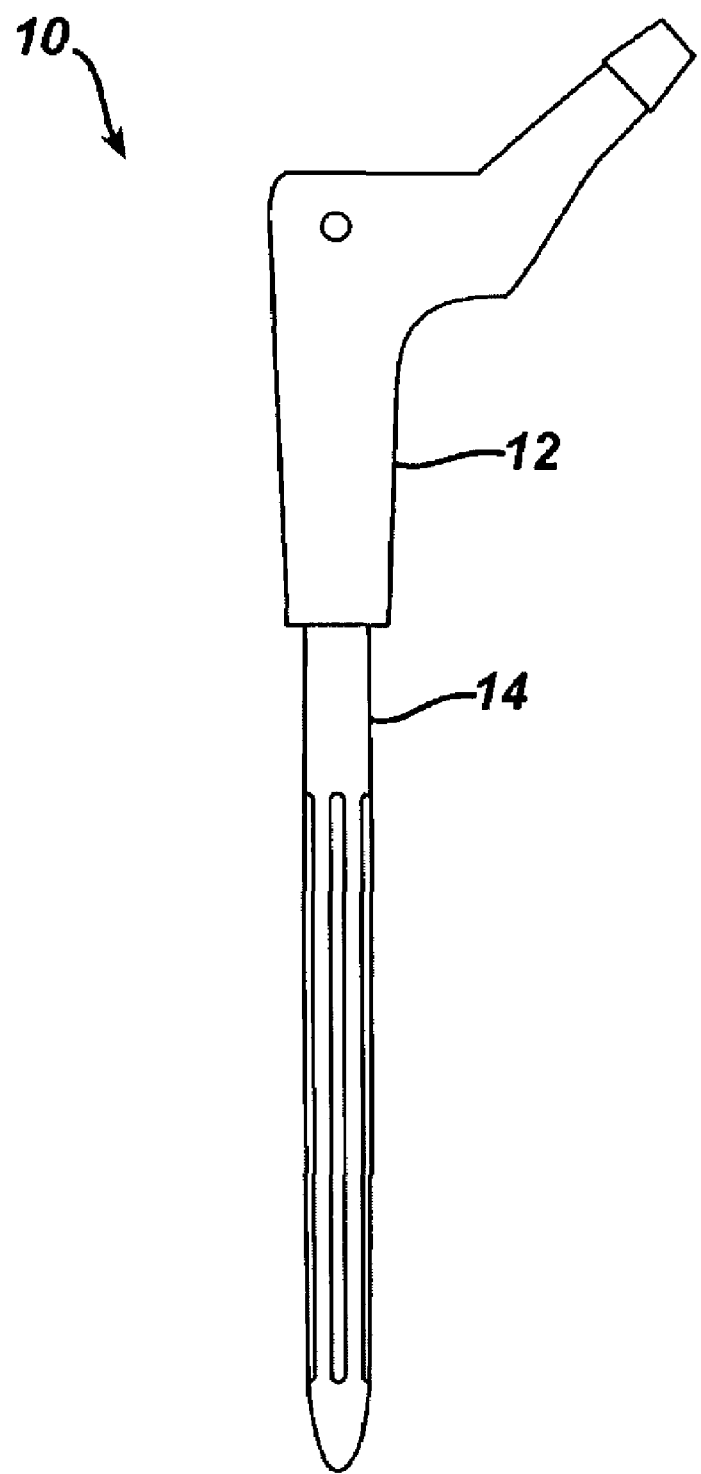
FIG. 16 is a plan view of a first embodiment of a modular hip stem for use in the medullary canal of a femur which may be aligned with the alignment device of the present invention.
Figure 18:
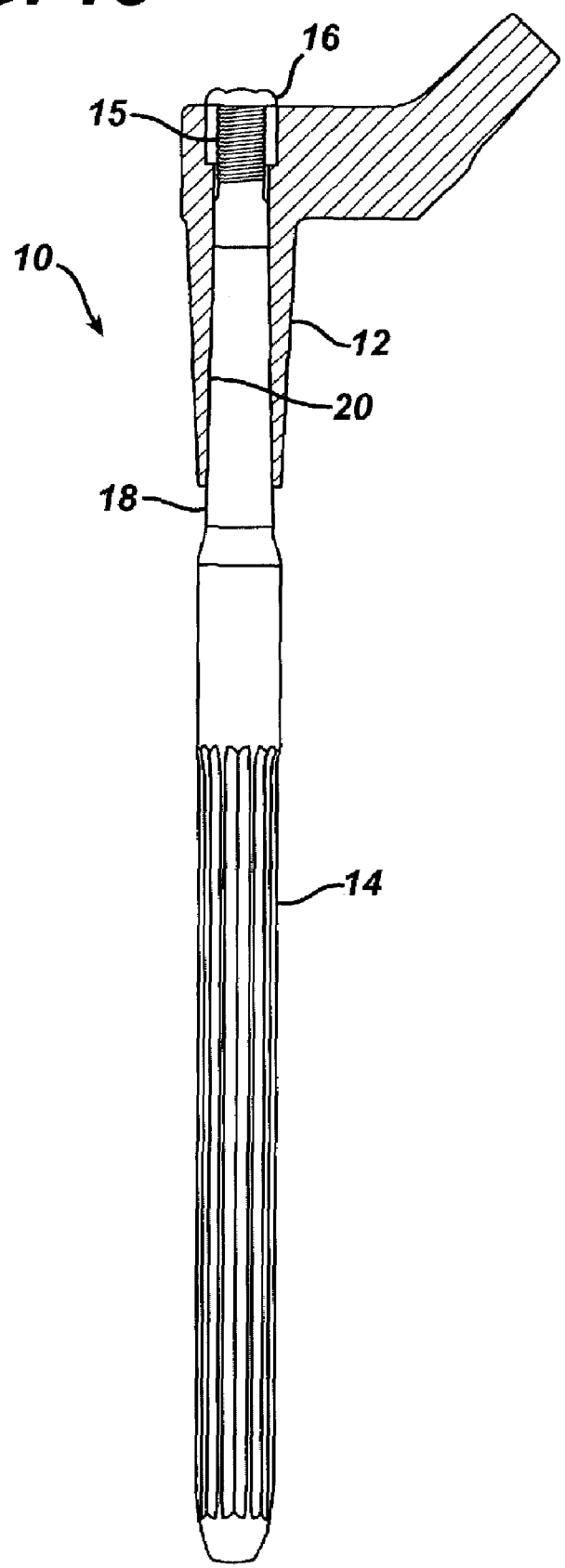
FIG. 18 is a plan view partially in cross-section of an alternative embodiment of a modular hip stem.
Figure 19:
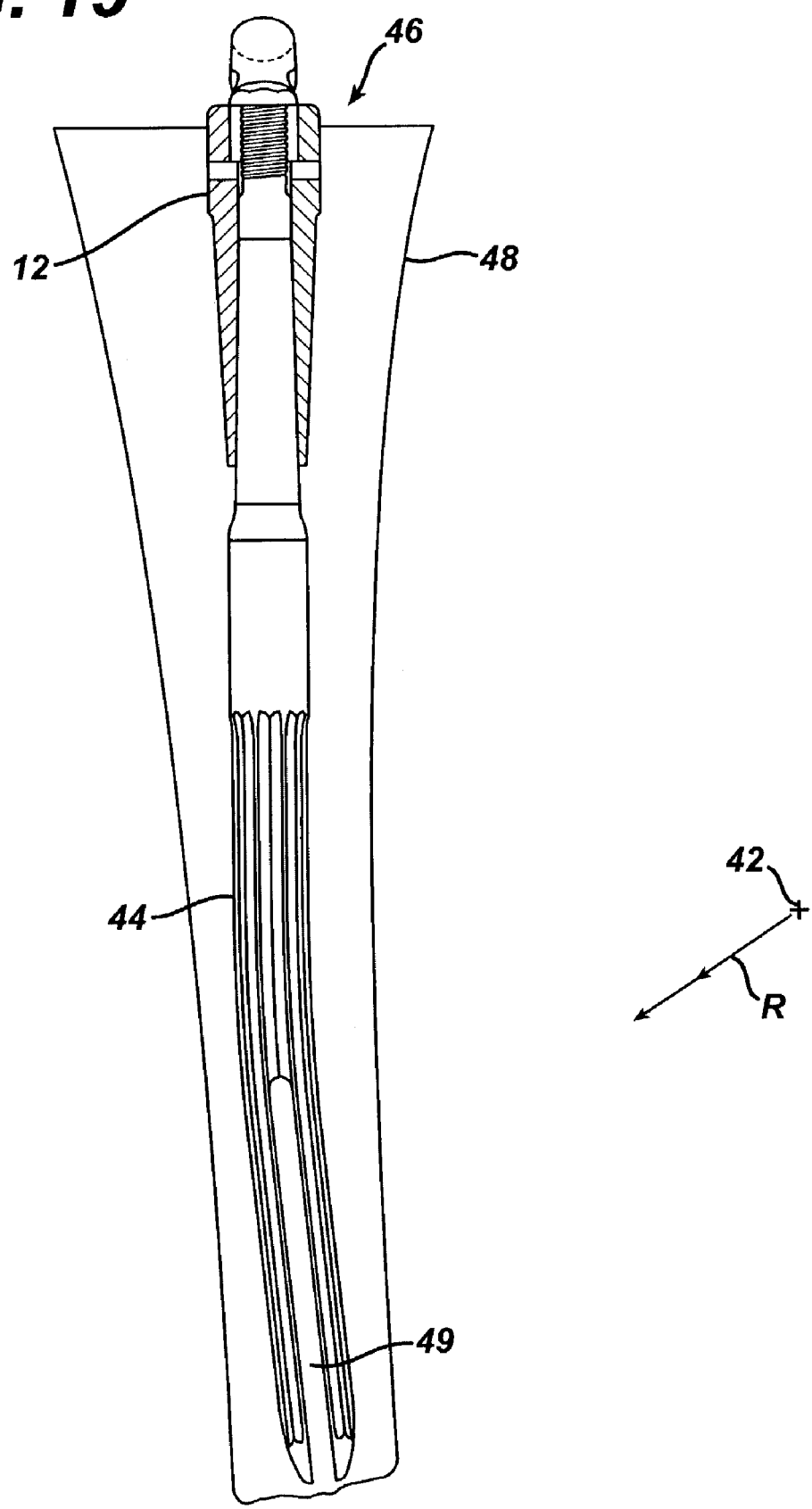
FIG. 19 is a side view partially in cross-section of the modular hip stem of FIG. 18.

Referring now to FIGS. 16 and 19, a hip stem 10 is shown. The hip stem 10 is suitable for use with the alignment instrument of the present invention. The hip stem 10 may be made of any suitable durable material which is compatible with the human body. For example, the hip stem 10 may be made of a titanium alloy, a cobalt chromium alloy, or a stainless steel alloy. As shown in FIGS. 16 through 19, the hip stem 10 includes a proximal body 12 and a bowed distal stem 14.

Referring now to FIG. 18, the proximal body 12 may be secured to the distal stem 14 in any suitable fashion. For example and as shown in FIG. 18, the proximal body 12 may be secured to the distal stem 14 by means of threads 15 located on the proximal portion of the proximal body 12 which are threaddedly engaged to a nut 16. In addition and as shown in FIG. 18, the distal stem 14 may include an external tapered portion 18 which mates with an internal tapered portion 20 of the proximal body 12. The taper of the internal tapered portion 20 and the external tapered portion 18 may be defined by an angle $\phi$. Preferably, the taper is self-locking and has an angle of $\phi$, for example, approximately 18 degrees or less.

Figure 17:
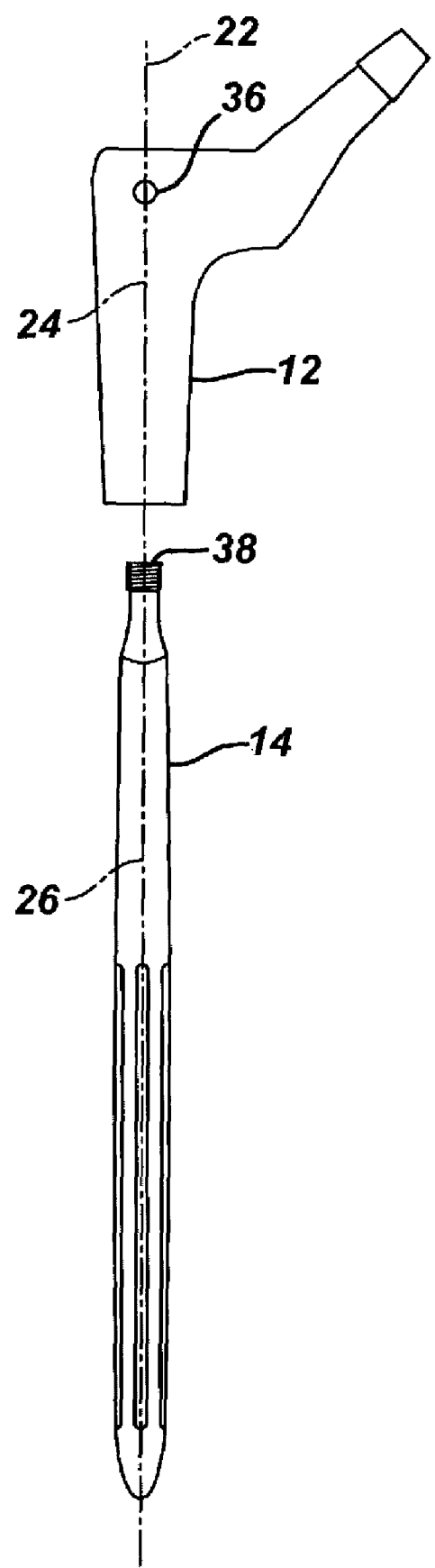
FIG. 17 is an exploded plan view of the modular hip stem of FIG. 16.

Referring now to FIG. 17, the proximal body 12 and the distal stem 14 may either or both be rotatable around longitudinal centerline 22. For example, the proximal body 22 may be rotatable in the direction of arrows 24 and the distal body may be rotated in the direction of arrows 26.

Figure 11:
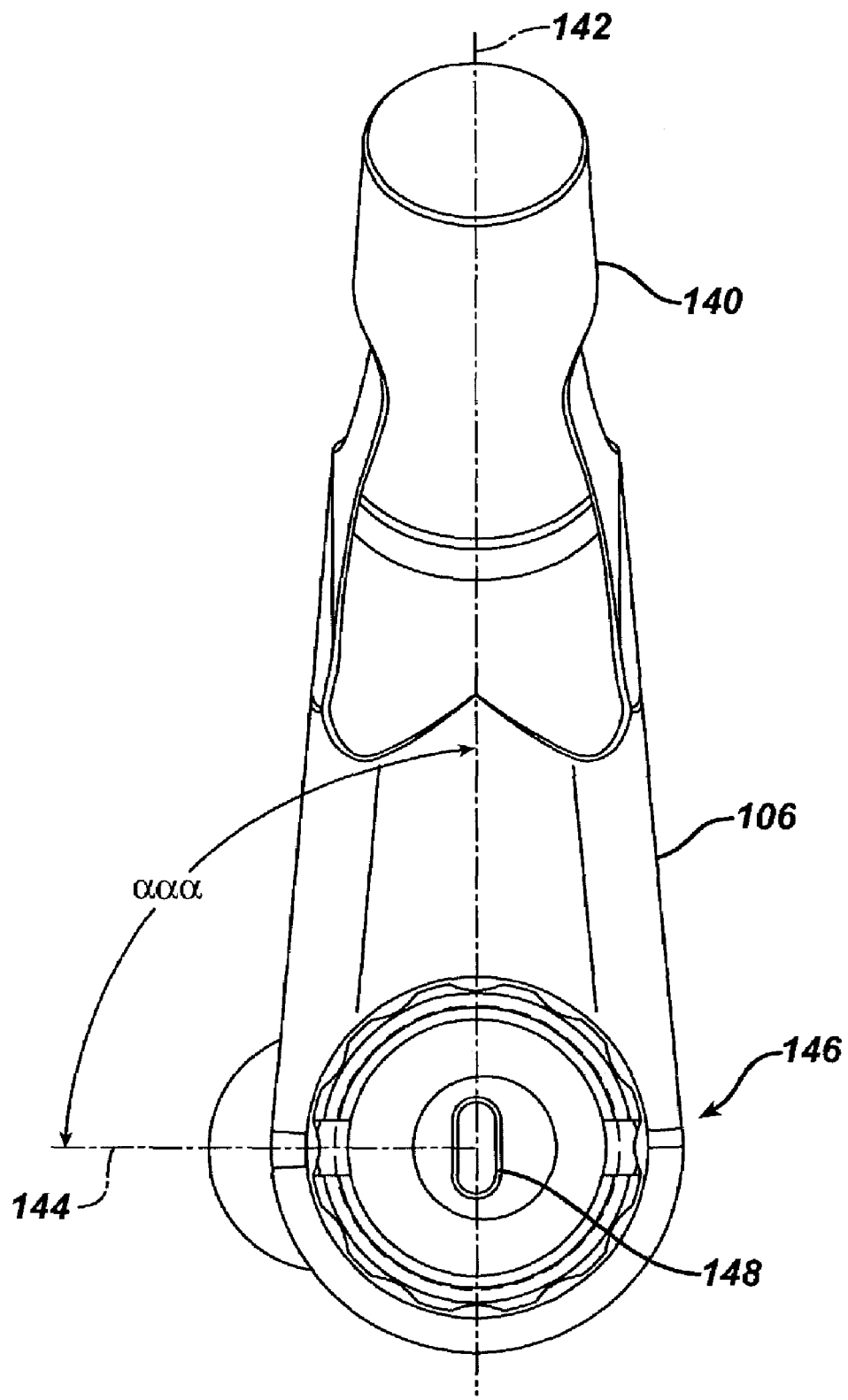
FIG. 11 is a top view of the modular trial of FIG. 10 showing the alignment keyway in greater detail.

Referring now to FIGS. 17C and 17D, a patient's femur is shown at 27. The natural femur has an anatomical anteversion. As shown in FIGS. 17C and 17D, the normal femur is also bowed anteriorly. In the present invention, the anatomic anteversion angle $\alpha$ is defined by a plane, shown at 29 in FIGS. 17C and 17D, through the anterior bow 31 of the femur and a line through the center of the femoral neck, shown at 33 in FIGS. 17C and 17D. The plane 29 corresponds with the position of the intramedullary canal. The arcuate top edge 35 of the plane shown in FIGS. 17C and 17D corresponds generally with the bow of the femur and intramedullary canal. Since the stem of the prosthesis will be received in the intramedullary canal, in the present invention the anatomic anteversion of the femur can provide the basis for setting the prosthesis anteversion. In the following description and drawings, the reference $\alpha$ is used for the anatomical anteversion angle as defined above; the reference $\alpha\alpha$ is used for the prosthetic or assembly anteversion angle. The prosthetic or assembly anteversion angle is defined by a plane through the bowed stem of the prosthesis and a line through the neck of the proximal part of the prosthesis. In at least one aspect of the present invention, a trial anteversion angle $\alpha\alpha\alpha$ between a plane through the bowed stem and neck of the trial can be based on data gathered preoperatively and can be adjusted by the surgeon intraoperatively to adjust the trial; the surgeon can use this data to assemble the modular implant. Such a trial anteversion angle $\alpha\alpha\alpha$ is illustrated in FIG. 11. Thus, through the use of the present invention, the surgeon should be able to assemble a prosthesis such that the prosthetic or assembly anteversion angle $\alpha\alpha$ approximates the anatomical anteversion angle $\alpha$. However, it should be understood that other landmarks could be used to determine the anatomic anteversion angle $\alpha$, and unless expressly called for in the claims, the present invention is not limited to any particular reference for the anatomic anteversion angle $\alpha$. For example, the anatomic anteversion angle could be determined from the position of the patient's foot with respect to the patient's shoulder line. It should also be understood that the principles of the present invention could also be applied to other prosthetic joints, such as shoulders, and the reference for the anatomic anteversion angle will depend on anatomic features of the bones comprising that joint. In addition, because of factors such as placement of the acetabular component of the prosthetic implant, the surgeon may determine that the optimum prosthetic anteversion angle $\alpha\alpha$ should vary somewhat from the anatomic anteversion angle $\alpha$. With the present invention, the surgeon can make such adjustments intraoperatively.

Referring now to FIG. 17E, the angular position between neck 32 of the proximal body 12 and the distal curved portion 34 of the curved distal stem 14 form the prosthetic anteversion angle $\alpha\alpha$. The prosthetic anteversion angle $\alpha\alpha$ affects the patient's ability to walk and his gait.

Figure 17A:
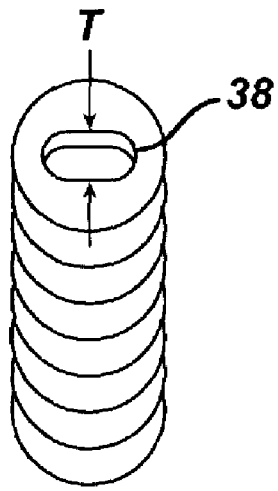
FIG. 17A is a partial perspective view of the distal stem of the stem of FIG. 17.
Figure 17B:
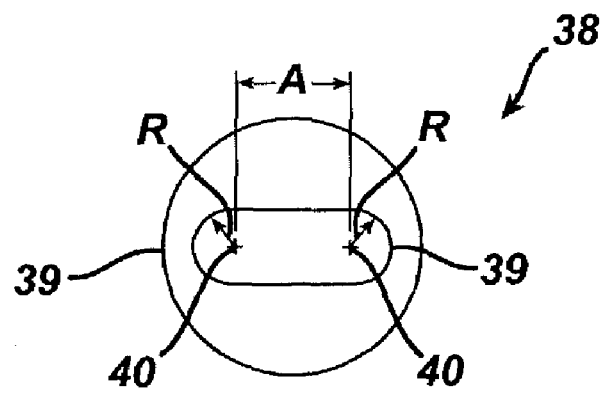
FIG. 17B is a partial plan view of the stem of FIG. 17.

As shown in FIG. 17, the hip stem 10 includes a proximal body location feature in the form of holes 36. Similarly, as shown in FIGS. 17A and 17B, the distal stem includes a distal stem location feature in the form of a slot 38. The proximal body location feature 36 and the distal stem location feature 38 may have any suitable shape and may be in the form of, for examples, slots, indents, triangles, squares, polygons, or any indexable feature.

Referring now to FIG. 17A and FIG. 17B, the slot 38 is shown in greater detail. As shown in FIG. 17B, the slot 38 may include two arcuate portions 39 defined by radius R extending from center points 40. The center points 40 may be spaced from each other a distance, for example A. The slot may have a depth T, of for example, 0.1 to 0.7 inches.

Referring now to FIG. 19, the distal stem 14 is shown in location where the arcuate shape of the distal stem is most pronounced. The curvature of the distal stem 14 may be defined by a radius R extending from distal stem center point 42. The distal arcuate stem 14 is fitted into arcuate portion 44 of the medullary canal 46 of the femur 48. The distal stem 14 may further include a slot 49 to assist in the positioning of the arcuate femur 48 into the arcuate medullary canal 46 of the femur 48.

Referring now to FIGS. 21, 22, 24, and 25, another embodiment of a hip stem for use in a hip prosthesis which may utilize the alignment device of the present invention is shown. Hip prosthesis assembly 50 includes stem 51. The stem 51 includes a proximal body 52 and a distal stem 54. Like the stem 10 of FIG. 16, the proximal body 52 of stem 51 may be secured to the distal stem 54 through an internal taper 62 in the proximal body 52 which is matable with the external taper 60 on the distal stem 54. It should be appreciated that the tapers 60 and 62 are preferably self-locking as in the stem 10. A ball or head 58 which mates with a cup (not shown) secured to a acetabulum (not shown) may be located on the proximal body 52. The distal stem 54 and the proximal body 52 may further be secured to each other by means of, for example, a nut 56 which is threadably engaged to a threaded portion 59 of the distal stem 54. Similar to the stem 10 of FIGS. 16 through 19, the stem 51 includes a first location feature 66 (shown in FIG. 23) associated with the distal stem 54 and a second alignment feature 53 associated with the proximal body 52.

Figure 23:
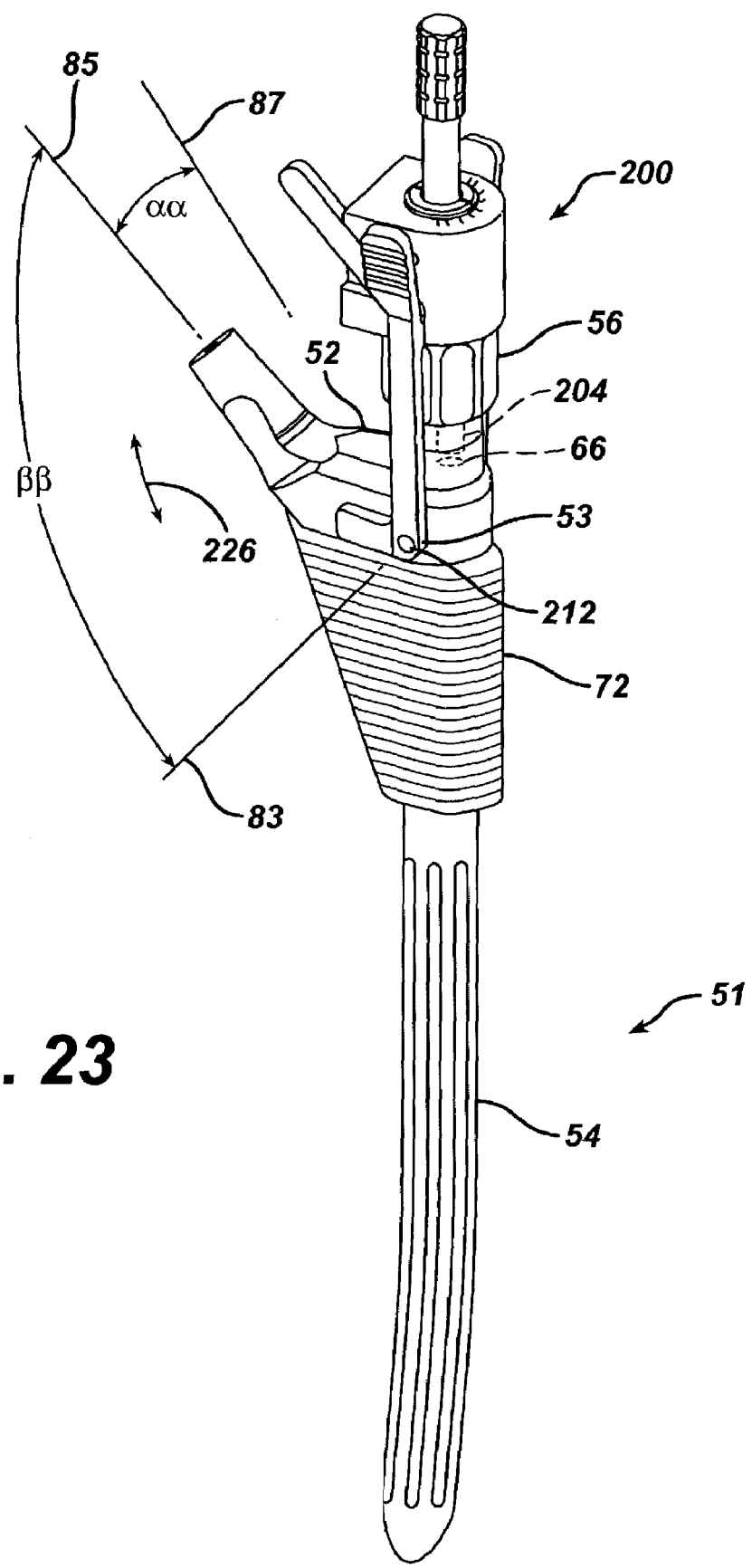
FIG. 23 is a perspective view an alignment device in use with the modular hip stem of FIG. 21.

The first alignment feature may be in the form of a recess 66 with a feature which can transmit torque. For example, the first alignment feature 66 may be in the form of a triangular opening, a rectangular opening, a Philips screw slot, a through slot or as shown in FIG. 23 in the form of a oval slot. The slot 66 of the stem 51 may be made to similar dimensions to that of slot 38 of the hip stem 10.

The hip stem 51 may include, in addition to the components already mentioned, a sleeve 72 which may mate with proximal body 52. The sleeve 72 may include a bore with an internal taper 74 which mates with external taper 76 on the proximal body 52. The sleeve 72 serves to provide additional support for the prosthesis 51 in the metaphyseal region and provides increased rotational stability for the prosthetic stem 51 when the stem is subjected to torsional loads.

The second alignment feature 53 may be in the form of a pair of opposed holes which are similar to the holes 36 of the hip prosthesis 10.

Figure 24:
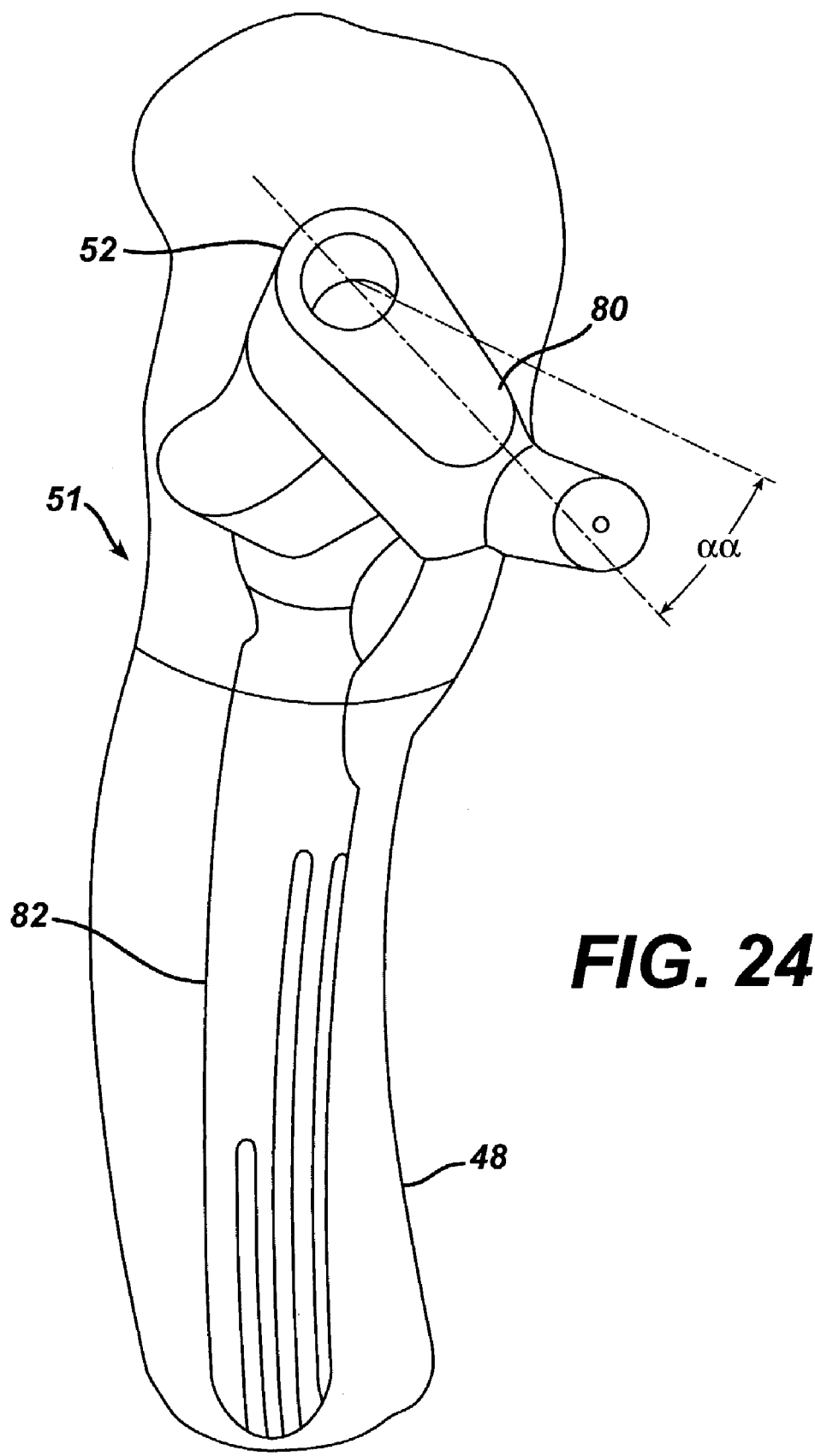
FIG. 24 is a perspective view of the modular hip stem of FIG. 21 shown in location in the medullary canal of a femur.
Figure 25:
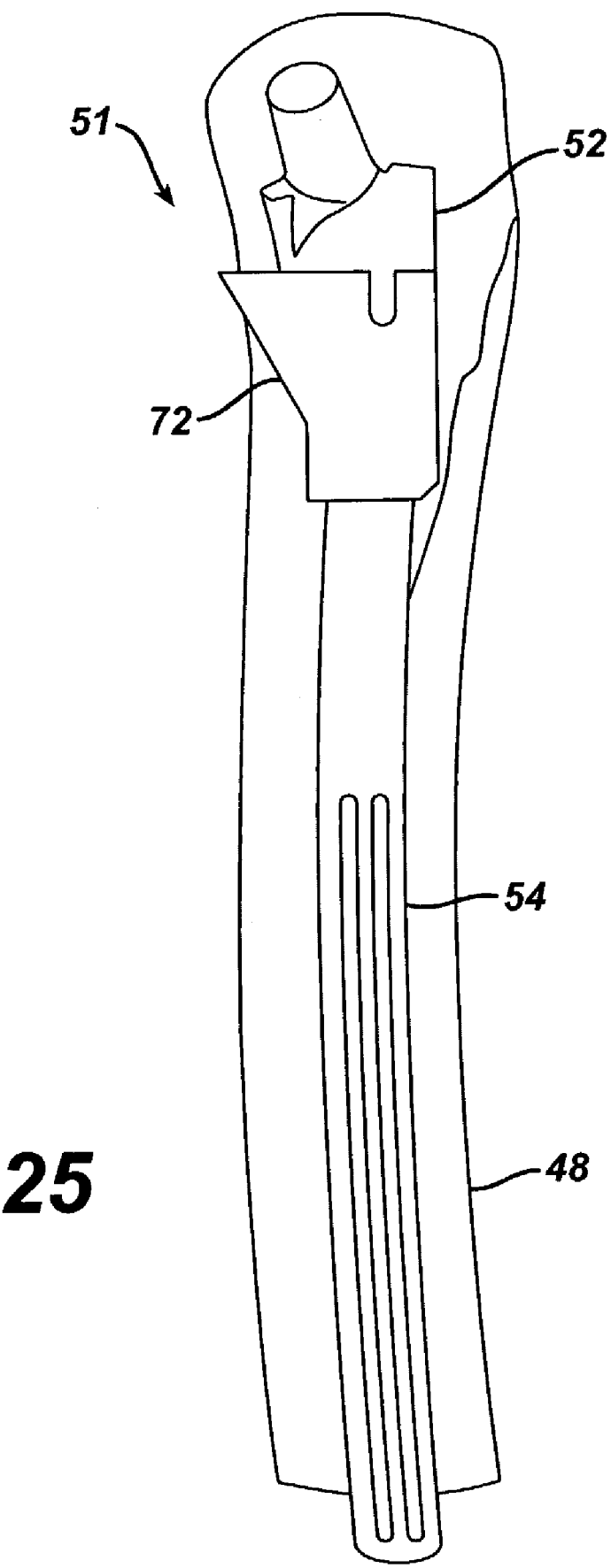
FIG. 25 is another perspective view of the modular hip stem of FIG. 21 shown in location in the medullary canal of a femur.

Referring now FIGS. 24 and 25, the hip stem 51 is shown in position in the long bone or femur 48. The proximal body 52 is shown in position with the neck 80 and the bowed portioned 82 of the distal stem 54 being out of angular alignment. The angle between the neck 80 and the arcuate portion 82 is defined as the prosthetic anteversion angle αα. It should be appreciated that in FIGS. 21 and 22, the distal stem 54 is shown out of angular position with the respect to normal femur geometry. The alignment device of the present invention permits the anteversion angle αα for the prosthesis 51 as well as the anteversion angle αα of the hip stem 10 of FIGS. 16 through 19 as well as the corresponding trials to be measured, and based upon a measured setting, the corresponding trial or implant to be set to that particular setting. Thus, utilizing this device, the anteversion angle can be accurately set on an implant or a trial.

Often orthopaedic surgeons utilize trials to place a substitute prosthetic item in the patient's body that can be removed after the trialing or verifying of the proper selection of the prosthesis. Once the dimensions of the trial are verified through reductions or movements of the patient's leg through the typical motions that the patient will require, the trial is removed and is sterilized to be used later for other surgeries. Conversely, a prosthetic implant once exposed to a patient is not utilized again. Therefore, it is important that the shape, position, and location of the appropriate trial be precisely duplicated by the actual implant. Thus, it may be very desirable to utilize an alignment device that can align a implant trial and preferably utilize the alignment determined by the implant trial and replicate the alignment in an implant.

Figure 9:
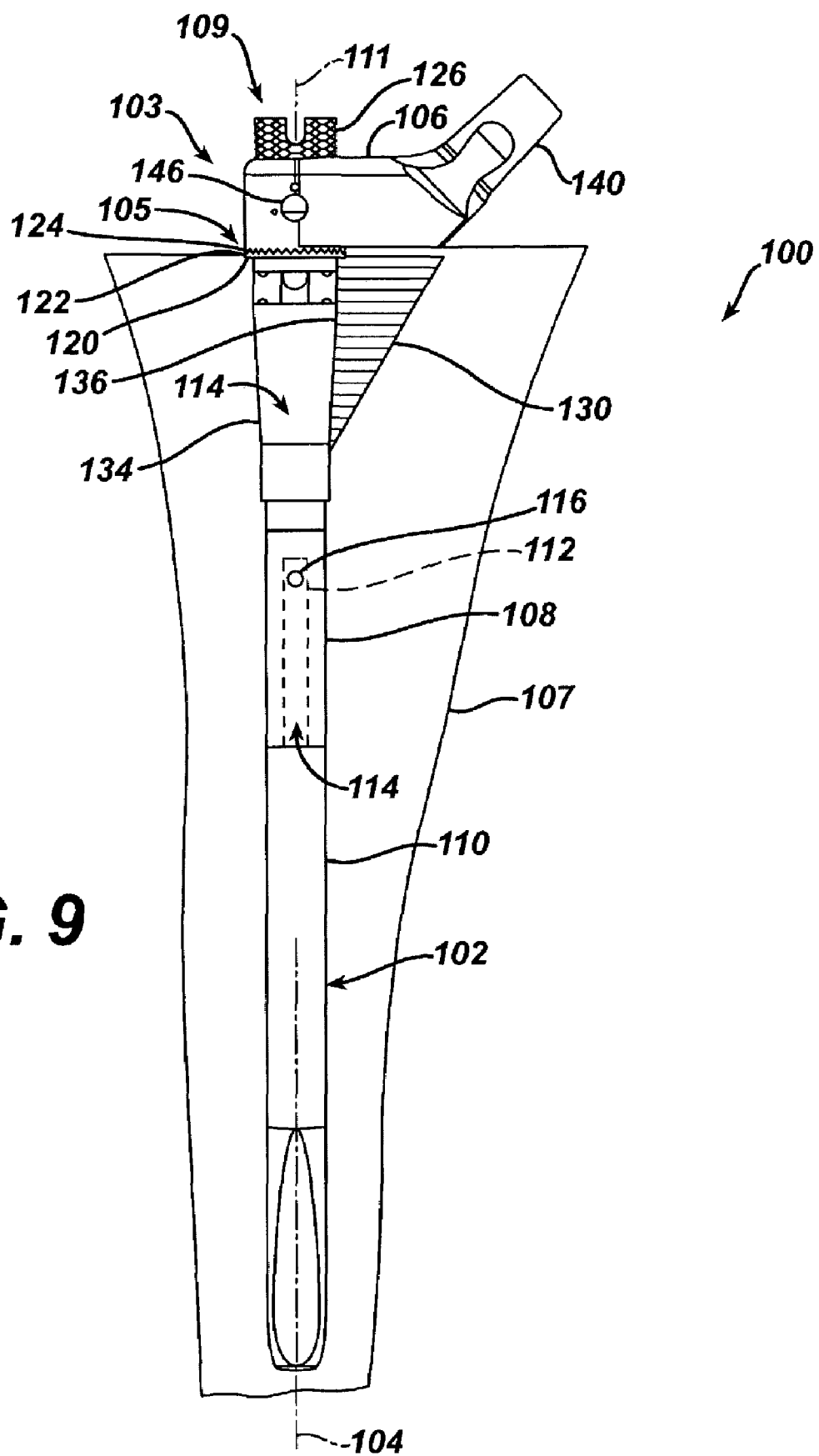
FIG. 9 is a plan view of a modular trial for use with the alignment device of the present invention.
Figure 10:
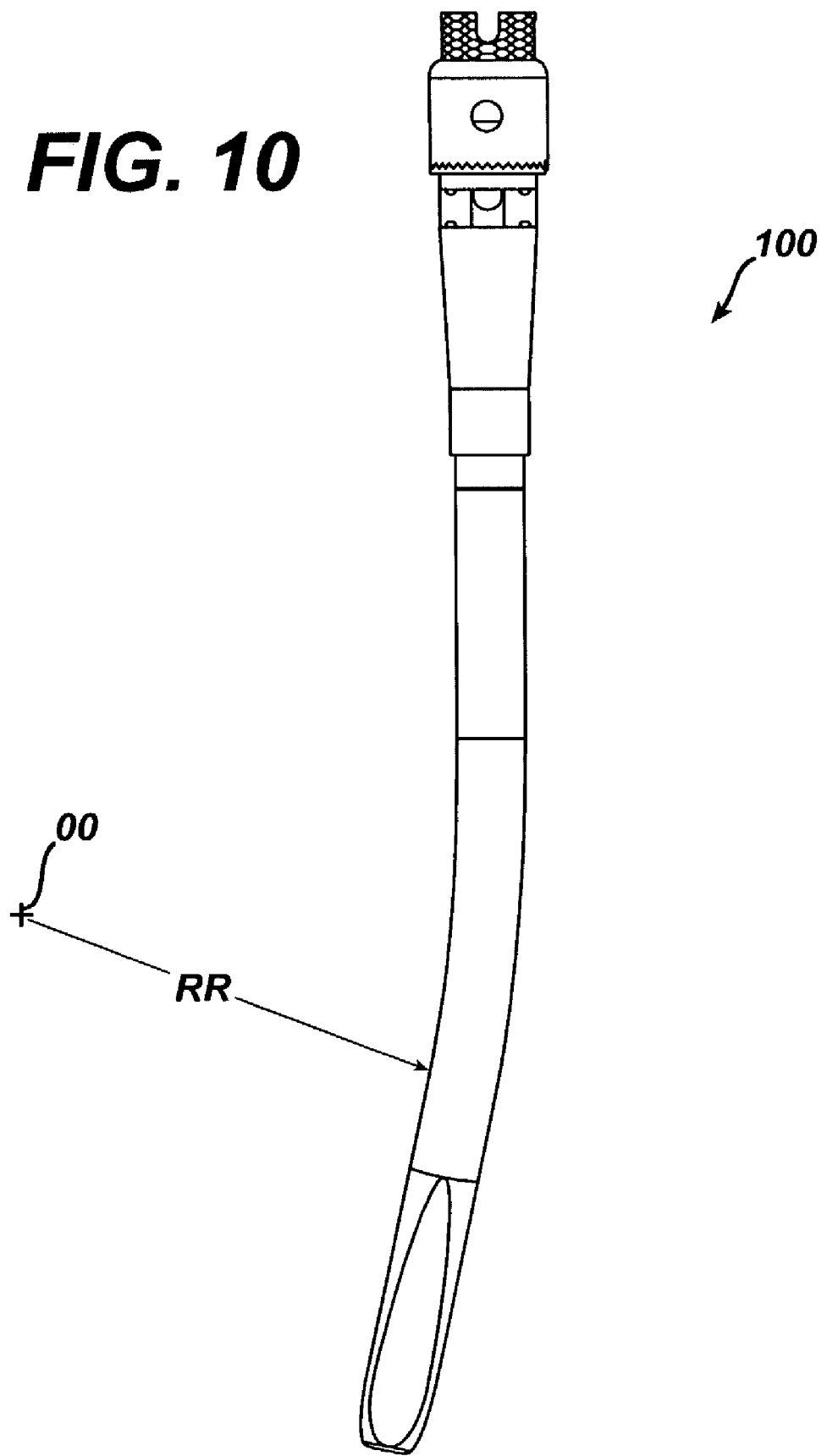
FIG. 10 is a side view of a modular trial of FIG. 10.

Referring now to FIGS. 9, 10, and 11, a trial 100 is shown which may be utilized with a alignment device of the present invention. The trial 100 includes a distal stem assembly 102 which is removably adjustably connected in a plurality of positions along longitudinal axis 104 of the distal stem assembly 102 to a neck trial 106.

The distal stem assembly 102 may include a proximal stem portion 108 which is connected to a curved distal stem portion 110. The proximal stem portion 108 and the curved distal stem portion 110 may be integral or, as shown in FIG. 9, the curved distal stem portion 110 may include a protrusion 112 which mates with a cavity 114 in the proximal stem portion 108. A pin 116 may be used to connect the proximal stem portion 108 to the curved distal stem portion 110.

The neck trial 106 is connected to the distal stem assembly 102 in such a way that the angular position along centerline 104 between the neck trial 106 and the distal stem assembly 102 may be adjusted. For example, as shown in FIG. 9, the curved distal stem portion 110 may include an index mechanism 120 which permits a fixed degree of rotation adjustment between the neck trial 106 and the distal stem assembly 102. The index mechanism 120 may include a first gear or spline 122, as shown in FIG. 9, rotatably keyed to the distal stem assembly 102. The index mechanism 120 may also include a second spline or gear 124 which may, as shown in FIG. 9, be integral with the neck trial 106. The gears 122 and 124 may be rotatably adjustable or movable with respect to each in increments of, for example, 10 degrees. Thus, the index mechanism 120 may provide for 36 different relative positions of the neck trial 106 with respect to the distal stem assembly 102. The gears or splines 122 and 124 are selectively engaged and disengaged by means of, for example, a nut 126 variably secured to the distal stem assembly 102.

Optionally, as shown in FIG. 9, the trial 100 may include a sleeve 130 which is used to replicate the sleeve 72 of the prosthesis 50, (see FIGS. 21 through 24). This sleeve 72 may be secured to the distal stem assembly 102 by a external tapered component 134 which forms a tapered sliding fit with the tapered bore 136 of the sleeve 130.

Referring now to FIG. 10, the curved distal stem portion 110 is shown with the curved distal stem 110 showing the full extent of the curve. The curved distal stem portion 110 may be defined by example a radius RR extending from an origin 00. The radius RR may be, for example, four to eight inches, and may vary depending on the curvature of the patient's femur medullary canal.

Referring again to FIG. 9, the neck trial portion 106 of the trial 100 may include a neck 140 to which a ball or head (not shown) may be used to fit against a acetabular cup (not shown) on the acetabulum of the patient (not shown).

Referring now to the FIGS. 10 and 11, the trial 100 preferrably includes locating features to determine the relative angular position ααα between neck centerline 142 and stem centerline 144. For example, the neck trial 106 may include a body locating feature 146 while the distal stem assembly 102 may include a stem locating feature 148. The body locating feature 146 may be in the form of, for example, opposed cylindrical holes. The stem locating feature 148 may be, for example, in the form of a key-way or oval shaped slot in the proximal end of the distal stem assembly 102.

Preferably, so that the trial 100 may be used with either or both the hip stem 10 or the hip stem 51, the holes 146 may be similar in size and location to the holes 53 of the stem 51 and the holes 36 of the hip stem 10. Similarly, the slot 148 of the trial 100 is preferably similar to the slot 38 of the prosthesis 10 and the slot 66 of the prosthesis 50.

Figure 1:
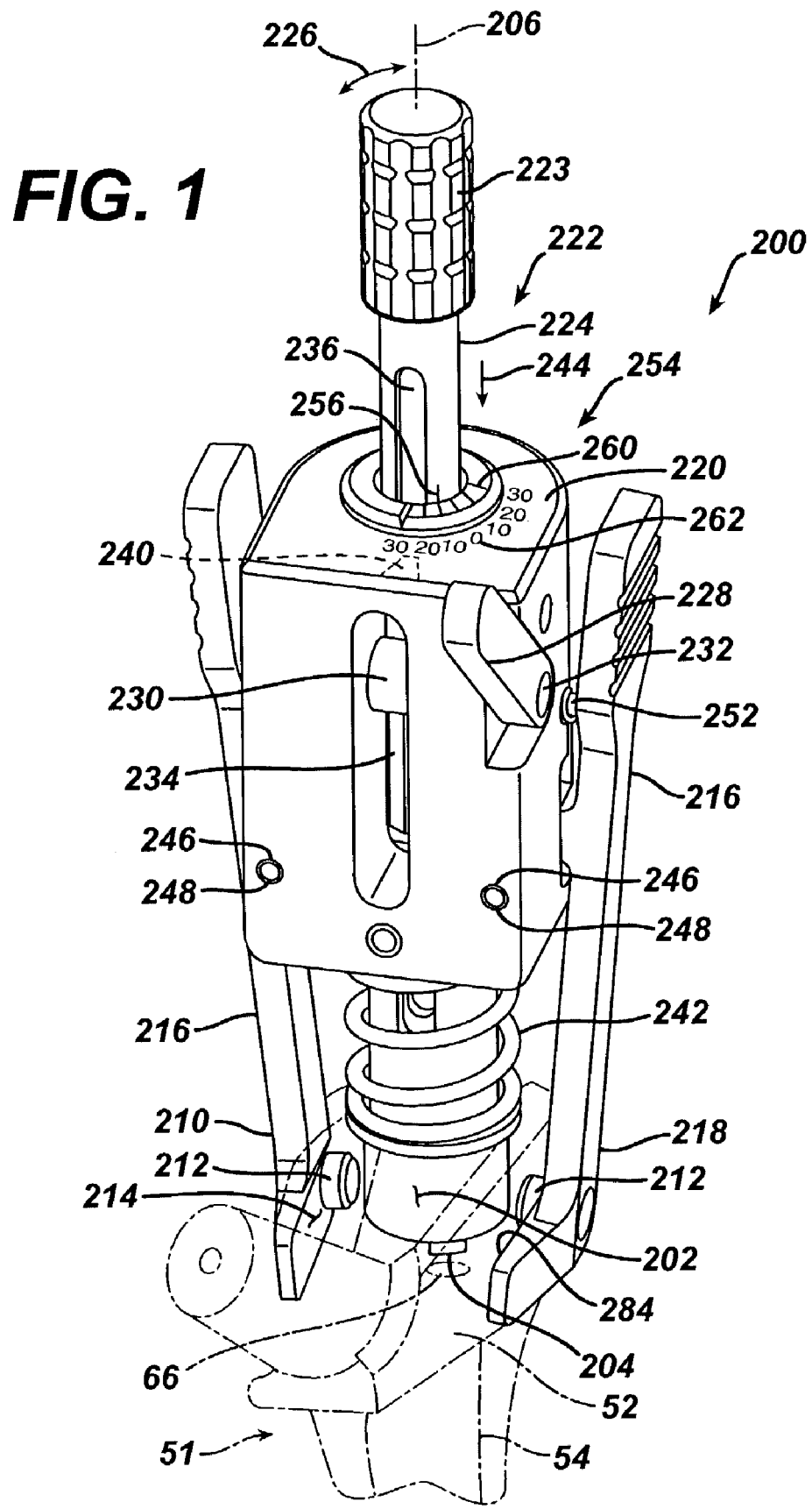
FIG. 1 is a perspective view of a first embodiment of an alignment device for aligning a prosthesis with respect to the canal of a bone for preparation of a total joint prosthesis implantation in accordance with the present invention.
Figure 2:
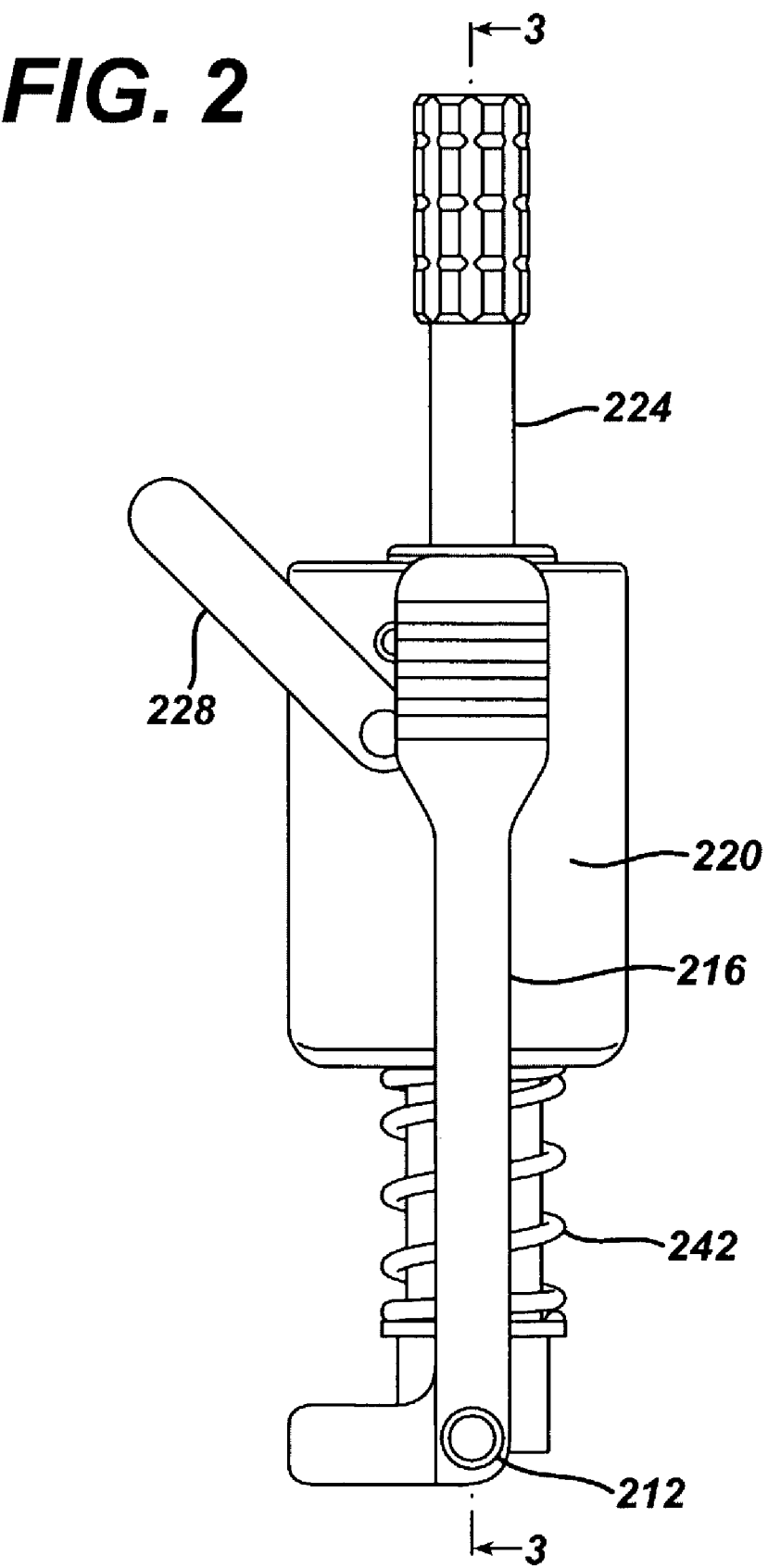
FIG. 2 is a side view of the alignment device of FIG. 1.

According to the present invention, and referring now to FIG. 1, an instrument 200 is shown. The instrument 200 may be utilized with either implants or trials. For example, the instrument 200 may be utilized with the trial 100 of FIGS. 10 and 11, or with the hip stem 10 of FIGS. 16 through 19. Likewise, the instrument 200 of the present invention may be used with the hip stem assembly 51 of FIGS. 21, 22, 24 and 25.

The instrument 200 is used in conjunction with the relative angular orientation of a first component of a multi-piece prosthesis to a second component of the multi-piece prosthesis. The instrument 200 may be utilized to observe the relative angular orientation of the components or to replicate the angular orientation of the first component relative to the second component. While the instrument 200 may be adapted for any of a large number of designs of prosthetic components and prosthetic trial components, including the hip stem 10, the hip stem 51 and the trial 100, the instrument 200 will for simplicity now be described for use with the hip stem 51 of FIGS. 21 and 22.

Continuing to refer to FIG. 1, the instrument 200 is utilized for at least one of observing or replicating the relative angular orientation of a first component, for example, proximal body 52, of a prosthesis with respect to a second component, for example, hip stem 54, of the prosthesis for use in joint arthroplasty. The instrument 200 includes a first member 202 for cooperation with the first component 52.

The first member 202 may have any suitable size and shape capable for cooperation with the first component 52. As shown in FIG. 1, the first member 202 may include a first member keyed feature 204. The first member keyed feature 204 cooperates with a first component key feature, for example, slot 66 of the first component 54. The key features 204 and 66 are used to angularly link the first member 202 with the first component 54. The key features 204 and 66 may have any suitable size and shape such that the first member 202 and the first component 54 are in timed engagement to provide a rotation and linkage of the first member 202 to the first component 54 about longitudinal centerline 206 of the instrument 200. The first member key feature 204 may be in the form, for example, of a recess or, as shown in FIG. 1, in the form of a protrusion. For cooperating with, for example, the slot 66 of the hip stem 50, the key feature 204 may be in the form of an oval protrusion. It should be appreciated that the keyed feature 204 may be a recess or a protrusion and may be, square, triangular, rectangular, a polygon or any shape capable of transmitting torque.

Figure 3:
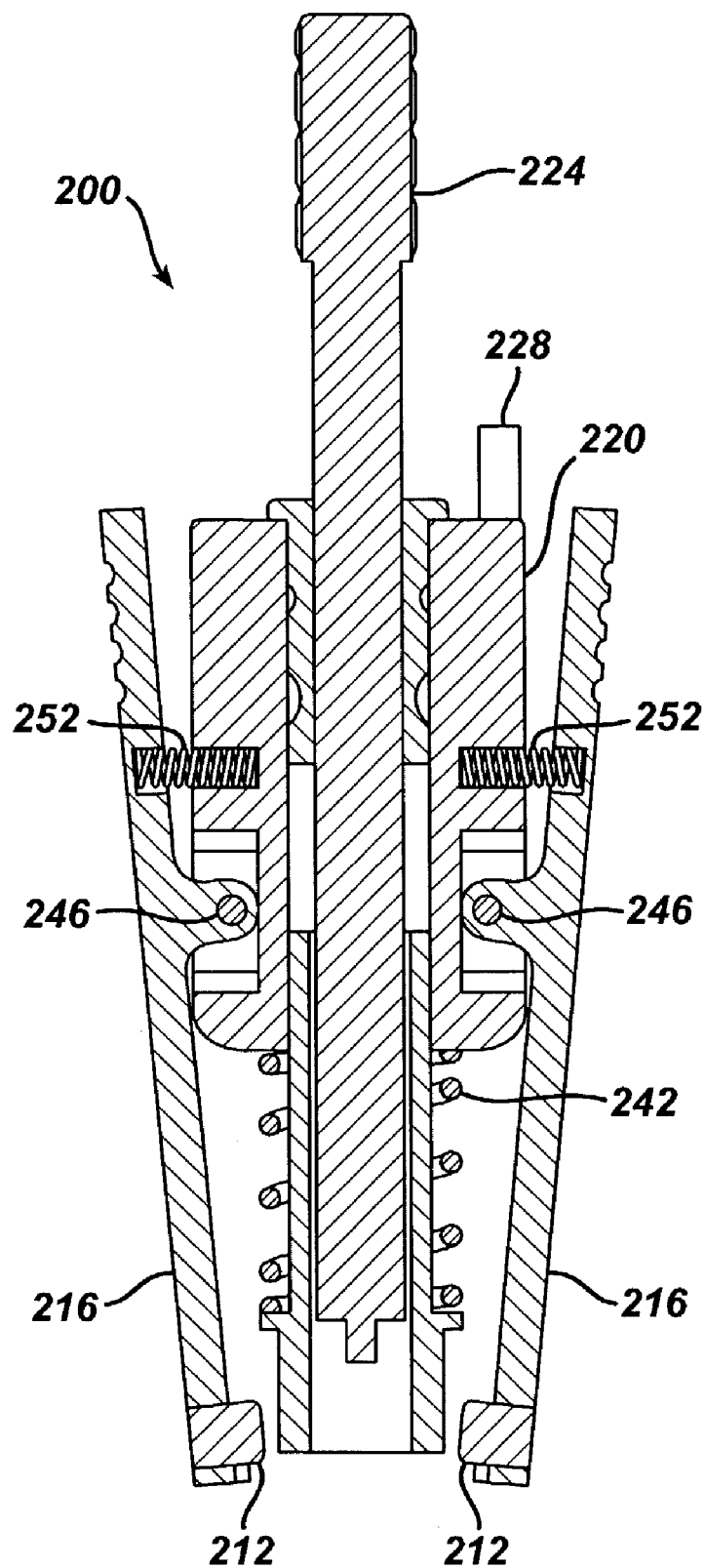
FIG. 3 is a cross-sectional view of the alignment device of FIG. 2 along the lines 3—3 in the direction of the arrows.
Figure 4:
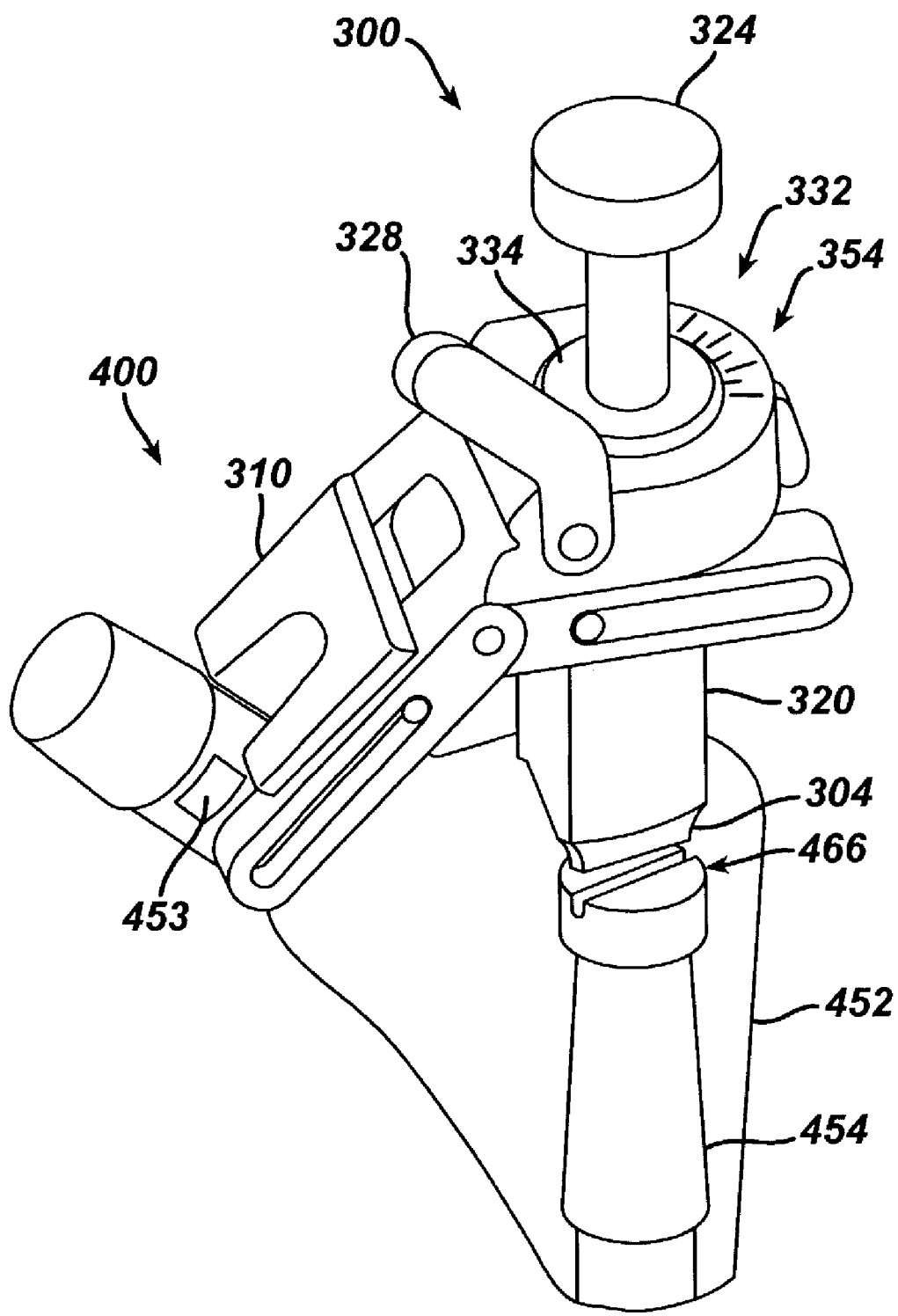
FIG. 4 is a perspective view of another embodiment of an alignment device in accordance with the present invention for aligning a prosthesis with respect to the canal of a bone shown mounted in position on a prosthesis.
Figure 4A:
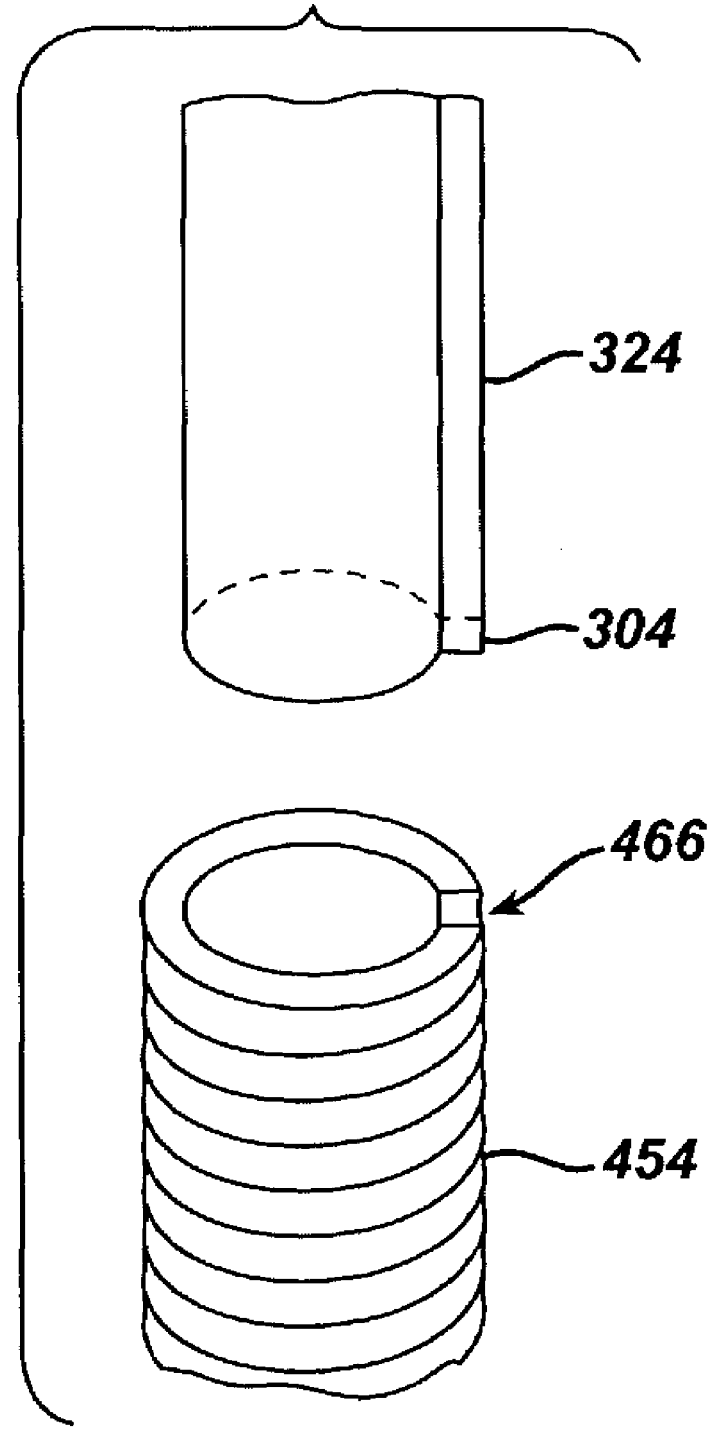
FIG. 4A is a partial perspective view of the alignment device of FIG. 4.

The instrument 200 further includes a second member 210 for cooperation with the second component 52. The second member 210 may be in cooperation with the second component 52 in any suitable manner. For example, the second member 210 may include a second member key feature 212, as shown in FIGS. 1 and 3, which cooperates with, for example, the second component key feature in the form of holes 53. The second member key feature 212 may have any suitable form and may, for example, be in the form of a pin 212, a flat 214 on arm 216, or in the form of a yoke (not shown).

For the instrument 200 to cooperate with the holes 53 in the hip prosthesis 50, the instrument 200 includes the pin 212 extending inwardly from the arm 216. To enhance the stability of the instrument 200, the instrument 200 may further include a stabilizing member 218 similar to the second member 210 but being a mirror image of the second member 210 to attach to the opposite side of the second component 52. The stabilizing member 218 also includes arm 216, pin 212 and flat 214.

Continuing to refer to FIG. 1, the instrument 200 further includes a feature 220 for cooperation with the first member 202 and the second member 210 for at least one of replicating or observing the relative angular orientation of the first component 54 with respect to the second component 52. The feature 220 may be in the form of, for example, a body. At least one of the first member 202 and the second member 210 are movably connected to the body 220. The body 220 serves the purpose of operably interconnecting the first member 202 to the second member 210. With the use of the body 220 the first member 202 may be positioned appropriately relative to the second member 210 to replicate or observe the relative angular orientation of the first component 54 with respect to the second component 52.

For example and as shown in FIG. 1, the body 220 may include a longitudinal opening 222 in which an orientation rod 224 is slidably movable along longitudinal axis 206. The first member key feature 204 may be located on an end of the orientation rod 224. The orientation rod 224 may include a gripping feature 223 in the form of, for example, flats, knurls or splines for assisting in attempting to move the orientation rod 224 axially along longitudinal centerline 206 and to rotate the orientation rod 224 in the direction of arrows 226.

As shown in FIG. 1, the orientation rod 224 and the key feature 204 may be angularly orientated with respect to the body 220 electively permitting and preventing the orientation rod 224 from rotating in the direction of arrows 226. Such selective rotation of the orientation rod 224 may be accomplished by any method.

For example, the body 220 may include a locking arm 228 connected to a cam 230 by shaft 232 mounted to the body 220. The cam 230 may be utilized to selectively lock the orientation rod 224 in a fixed position with respect to the body 220 or, as shown in FIG. 1, may merely prevent the orientation rod 224 from rotating in the direction of arrows 226.

In order that the locking arm 228 may be utilized to prohibit rotation in the direction of arrows 226 while permitting the movement of the orientation rod 224 along the axis of the longitudinal centerline 226, the body 220 may further include a bushing or sleeve 234. The sleeve 234 is rotatably fitted to the opening 222 in the body 220. The cam 230 selectively engages the sleeve 234 to prevent and permit relative rotational motion of the sleeve 234 with respect to the body 220. The sleeve 234 may be operably connected to the orientation rod 224 such that the orientation rod 224 may move along the longitudinal axis 206 but be prohibited from relative motion with respect to the sleeve 234 rotationally in the direction of arrow 226.

One method, as shown in FIG. 1, of preventing rotation of the orientation rod 224 with respect to the sleeve 234 is by providing, for example, a longitudinal groove 236 in the orientation rod 224 which cooperates with a protrusion 240 extending inwardly from the sleeve 234. To keep the key feature 204 of the orientation rod 224 in full engagement with the slot 66 of the hip prosthesis 50, the instrument 200 may include a spring 242 positioned between the orientation rod 224 and the body 220 to urge the orientation rod 224 and the key feature 204 downwardly in the direction of arrow 244.

As shown in FIG. 1, the second member 210 is rotationably fixedly secured to the body 220 about longitudinal axis 206. To assure that the pin 212 is fully engaged in hole 53 of the prosthesis 50, the arm 216 may, as shown in FIG. 1, pivot about pin 246 secured at hole 248 of the body 220. Similarly, the stabilizing member 218 engages the other hole 53 if first component 54 at pin 212 and is pivotally positioned with respect to the body 220 at pin 246 secured to hole 248 in the body 220. The second member 210 and the stabilizing member 218 are preferably urged in the direction of arrows 250 toward the second component 52 by means of springs 252 positioned between the arm 216 and the body 220.

To measure the relative position of the first member 202 with respect to the second member 220 and correspondingly, the relative angular position of the first component 54 to the second component 52, the instrument 200 may include indicia 254 located on the instrument 200 to provide a measuring scale for the relative position of the first member 202 with respect to the body 220.

The indicia 254 may have any suitable size and shape capable of providing the measurement capability for the instrument 200. The indicia 254 may, for example, include a single indicia in the form of a mark 256 extending axially along orientation rod 224. The indicia 254 may further include a plurality of indicia in the form of body indicia 260 located on the sleeve 234 of the body 220. The indicia may be in the form of characters, such as letters, or numbers, as shown at 262 in FIG. 1. Numbers 262 may be located adjacent their respective body indicia 260. The numbers 262 may correlate to, for example, a particular degree of anteversion.

Figure 12:
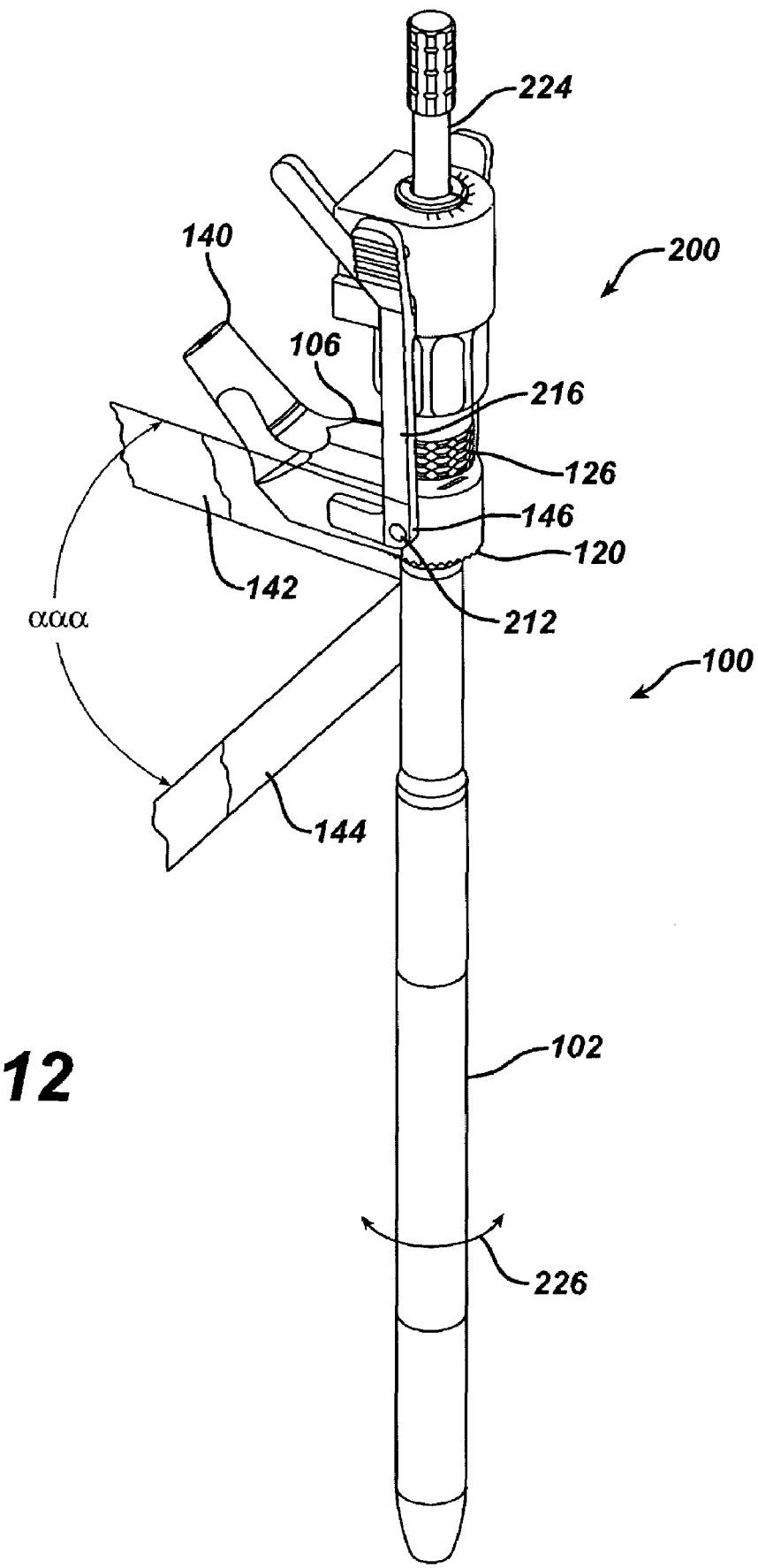
FIG. 12 is a perspective view of the alignment device of FIG. 1 shown in engagement with the modular trial of FIG. 10.
Figure 13:
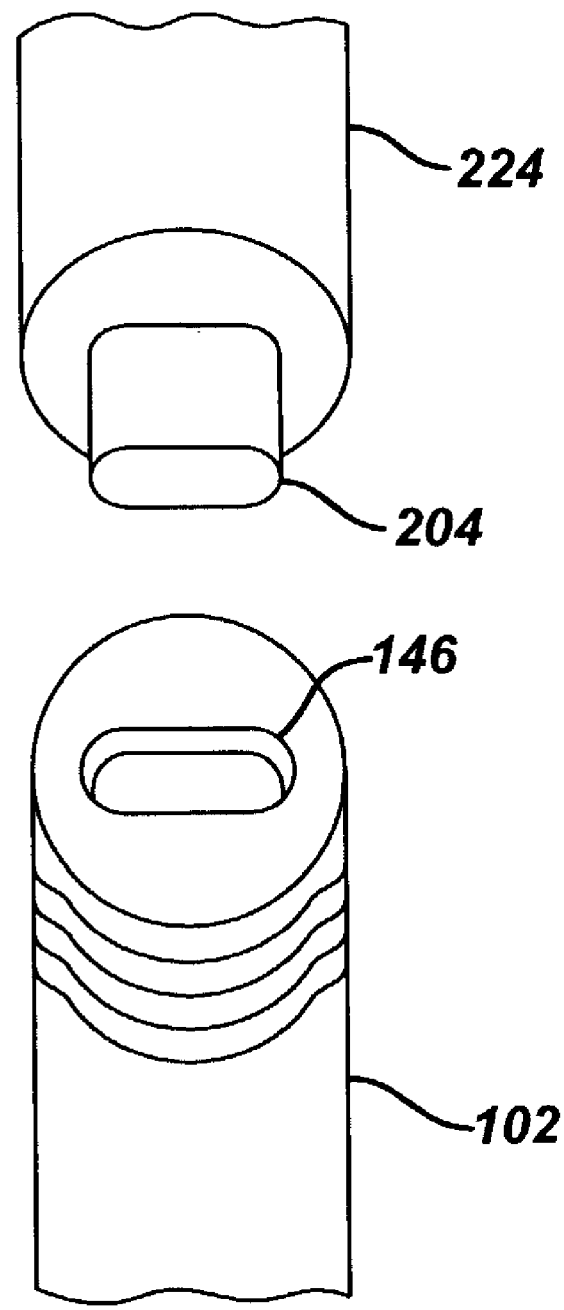
FIG. 13 is a partial perspective view of FIG. 12.
Figure 20:
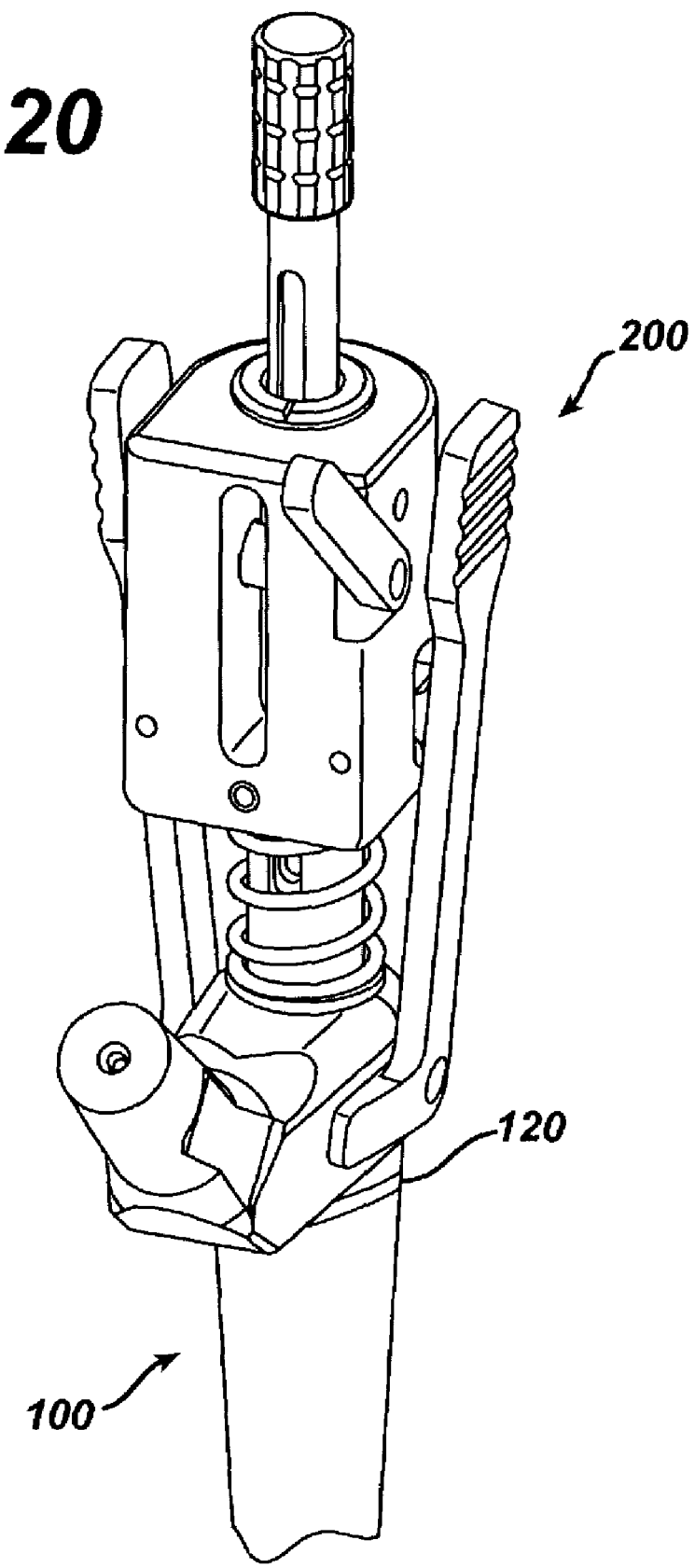
FIG. 20 is a perspective view of the alignment device of FIG. 1 shown in engagement with the modular hip stem of FIG. 18.
Figure 21:
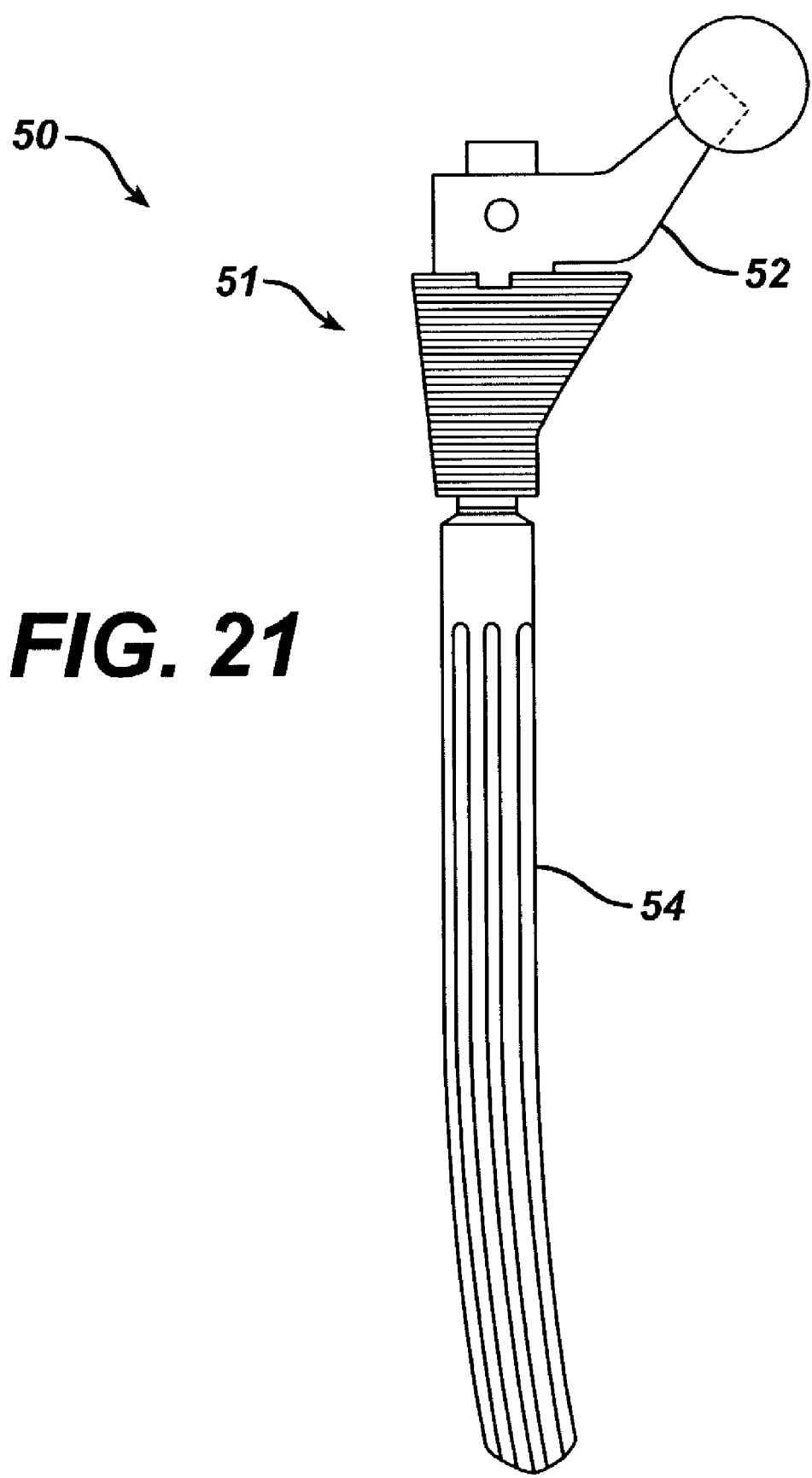
FIG. 21 is a plan view of another embodiment of a modular hip stem for use in the medullary canal of a femur which may be aligned with the alignment device of the present invention.
Figure 22:
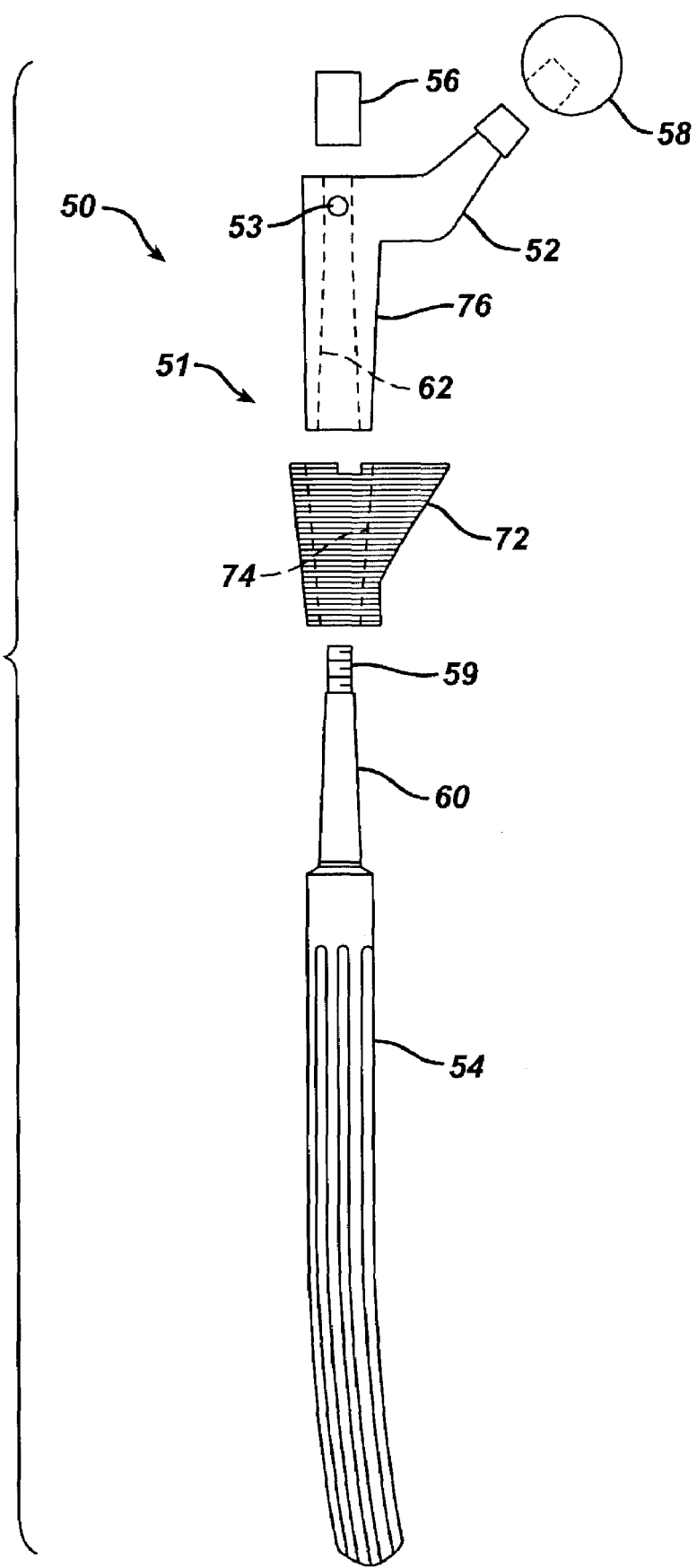
FIG. 22 is an exploded plan view of the modular hip stem of FIG. 21.

Referring now to FIG. 12, FIG. 13 and FIG. 20, the instrument 200 of the present invention is shown in location on trial 100. The instrument 200 is secured in position on the trial 100. The pins 212 on the arm 216 are engaged in the holes 146 of the neck trial 106 of the trial 100. Similarly, the key 204 of the orientation rod 224 of the instrument 200 is engaged in slot 146 of the stem assembly 102 of the trial 100. By loosening the nut 126 from the stem assembly 102, the neck trial 106 may rotate in the direction of arrows 226 with respect to the distal stem assembly 102. Stem centerplane 144 and the neck centerplane 142 define an included angle of the trial 100, which corresponds with the trial anteversion angle ααα.

By radiograph, CT scan or other imaging technique a patient's anatomic anteversion angle α may be determined. In typical cases, this anatomic anteversion angle α will be the optimum prosthetic anteversion angle αα. The trial 100 may be set by the instrument 200 so that the trial anteversion angle ααα equals the optimum anteversion angle of, say, for example, 90 degrees. Once the optimum trial anteversion angle of ααα has been determined and set, the nut 126 may be tightened onto the distal stem assembly 102, causing the index mechanism 120 to securely lock. Once securely locked, the index mechanism 120 may prevent the rotation of the neck 140 with respect to the distal stem assembly 102.

It should be appreciated that the indicia 254 on the instrument 200 may be utilized either to set a predetermined anteversion angle determined by radiograph, CT scan, other imaging technique or by a common preset anteversion angle. It should be appreciated by utilizing the instrument 200 and the trial 100, the neck trial 106 may be rotated with respect to the distal stem assembly 102 an increment based on the index mechanism 120 of perhaps 10 degrees or less.

For example, the trial 100 may be preset utilizing instrument 200 to a particular first trial anteversion angle ααα. The trial 100 may then be inserted into a patient and a trial reduction performed. If the trial reduction indicates that the trial anteversion angle ααα should be increased or decreased, the nut 126 may be loosened enough to permit rotation of the index mechanism 120 and the proper amount of change of anteversion can be set by utilizing the indicia 254 and the instrument 200 or by merely listening to clicks as the index mechanism 120 is indexed appropriate number of teeth, with each tooth movement representing, for example, 10 degrees.

Figure 14:
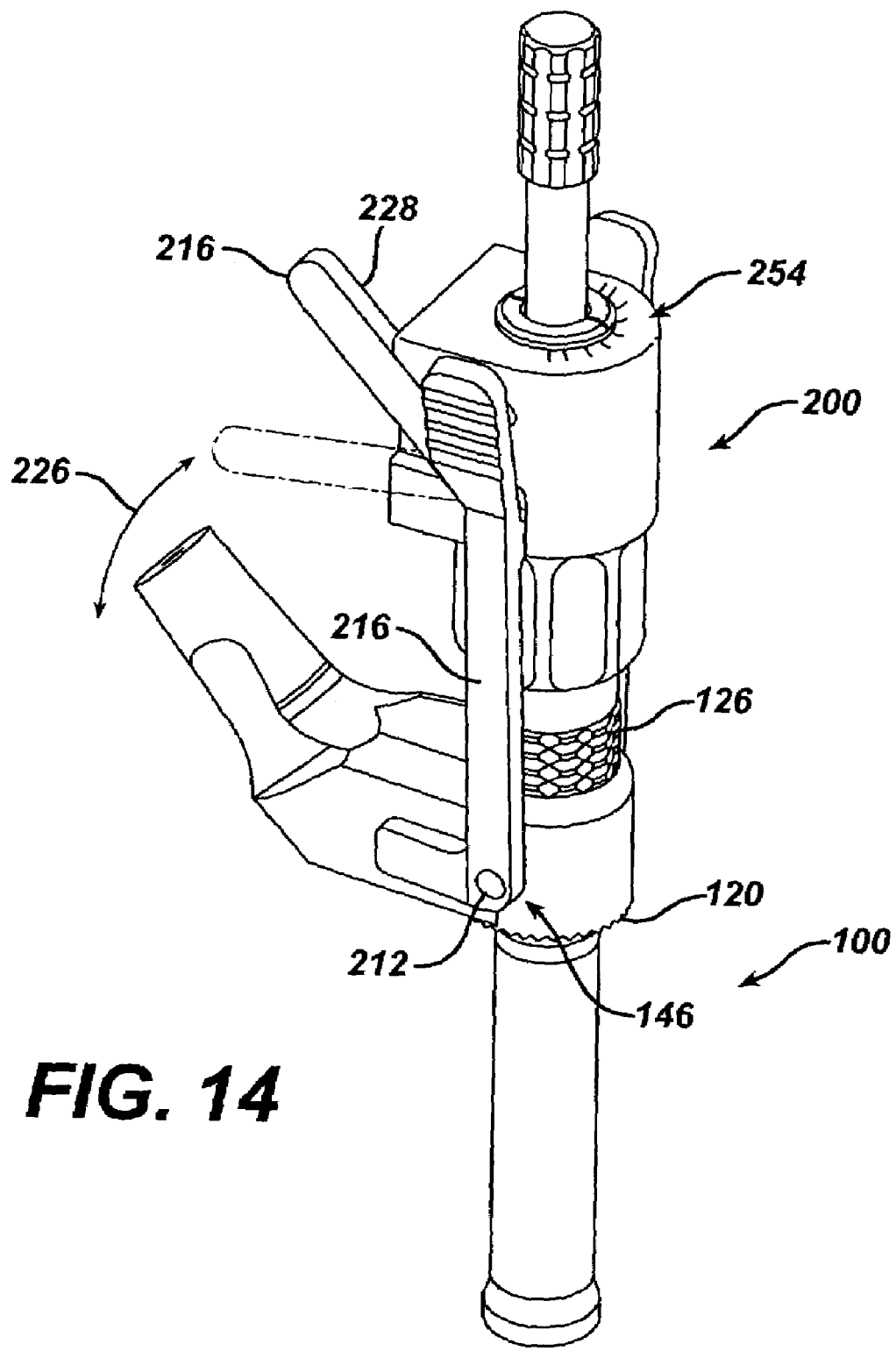
FIG. 14 is a partial perspective view of the alignment device of FIG. 1 shown in engagement with the modular trial of FIG. 10.
Figure 15:
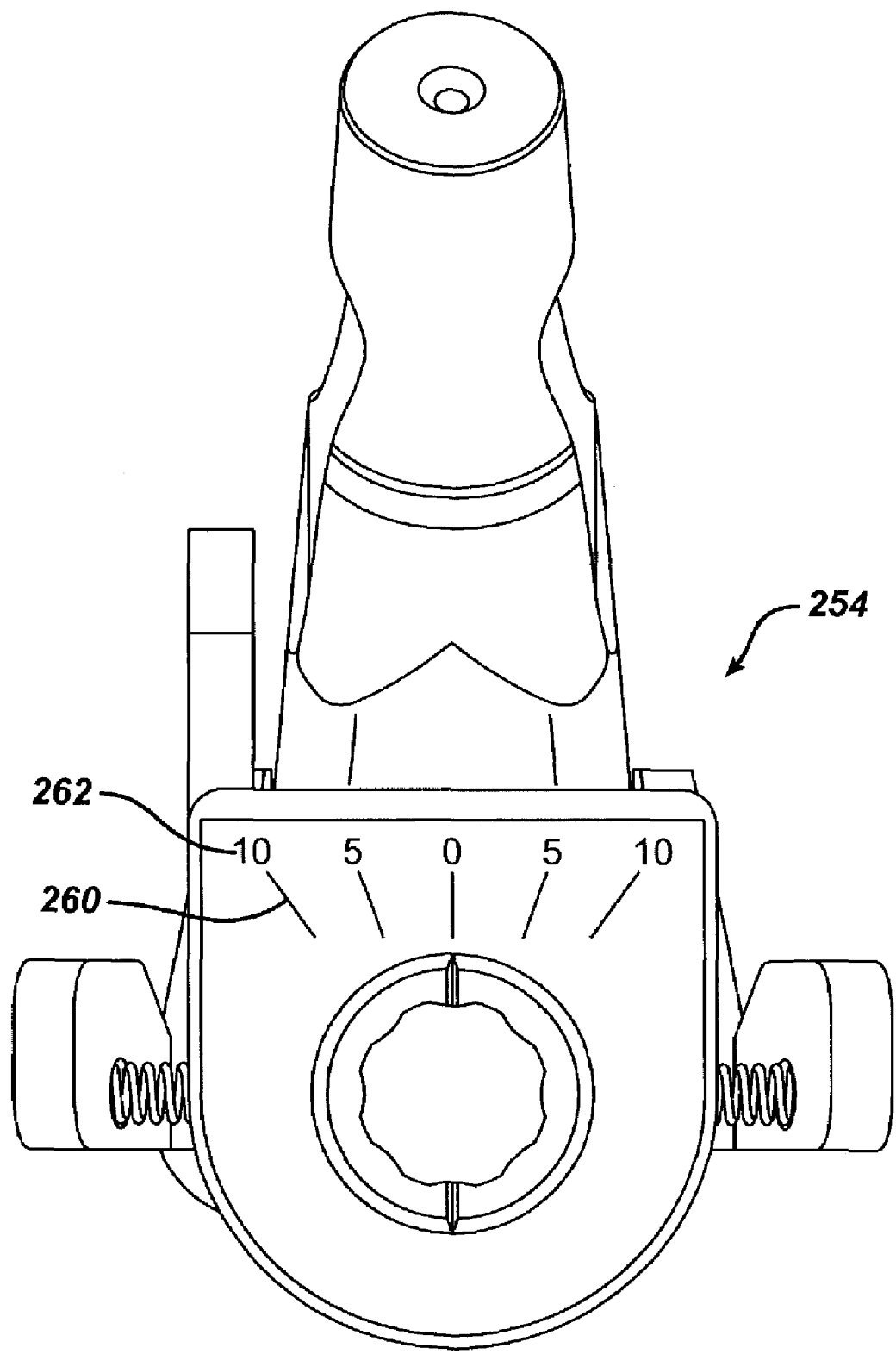
FIG. 15 is a top view of the alignment device of FIG. 1 shown in engagement with the modular trial of FIG. 10.

Referring now to FIG. 14 and FIG. 15, once the ideal anteversion is determined through the use of the trial 100 in the patient, the clinically selected correct anteversion can be measured by use of the instrument 200. Once the trial 100 is set in the proper position, the instrument 200 may be positioned into the trial 100 and the locking arm 228 moved from its unlocked position (shown in solid) to its locked position (shown in phantom). Once the instrument 200 is locked in a desired setting, this desired setting may be repeated on, for example, an implant by reading the setting on the indicia 254 or by maintaining the instrument 200 in its locked position and utilizing the instrument 200 to properly preset an implant or stem prosthesis.

Referring now to FIG. 23, the instrument 200 is shown in position on prosthetic hip stem 51. It should be appreciated that the instrument 200 may be similarly used on hip stem 10 of FIGS. 16 through 19. It should also be appreciated that the instrument 200 may also be used with monolithic stems. Once the proper anteversion is determined by the instrument 200, a monolithic can be used with the determined anteversion.

Before the instrument 200 is installed onto the hip stem 51, the proximal body 50 is loosely fitted to the distal stem 54. The neck 56 and body 52 are loosely fitted onto the distal stem 54 so that the proximal body 52 may rotate in the direction of arrows 226 with respect to the distal stem 54. In this rotatable assembly condition of the hip stem 51, the instrument 200 is engaged with the hip stem 54. The proximal body 52 will need to be rotated in the direction of the arrows 226 with respect to the distal stem 54 so that the key 204 may completely seat into the slot 66 of the distal stem 54 and so that the pin 212 may fully seat into the holes 53 in the hip proximal body 52. Once the instrument 200 is fully seated into the hip stem 51, the distal end of the distal stem 54 may be slightly tapped in an upward direction to seat the proximal body 52 to the hip stem 51.

Since the angle between the axis 83 of the pin 212 and the neck centerline 85, shown at ββ in FIG. 23, is fixed, and since the position of the axis 83 of the pin with respect to the hip stem 54 is set by the locked instrument 200, the implant can be fixed with the proper anteversion angle between the neck centerline 85 and a plane 87 through the anterior bow of the stem 56. In this secured and tapped position, the centerline neck centerline forms the prosthetic anteversion angle αα with the plane 87. Through the use of the instrument 200, the prosthetic anteversion angle αα is virtually identical to the trial anteversion angle ααα of the trial. (See FIG. 12) And since the plane 87 will correspond with the plane 29 through the anterior bow of the femur (See FIGS. 17C and 17D) when the prosthetic is implanted, proper orientation of the prosthetic head and neck can be achieved.

After the proximal body has been seated temporarily into the distal stem 54, the instrument 200 may be removed. After removal of the instrument 200, the proximal body 54 may be securely seated onto the distal stem 54 by using tools (not shown) to fully lock the tapers 18, 20 and torque the nut 56 to the distal stem 54 finalizing the assembly of the stem 51.

Referring now to FIGS. 4 through 8, an alternate embodiment of the present invention is shown as orientation device 300. Orientation device 300 is similar to the orientation device 200 of FIG. 1. The orientation device 300 includes a body 320 which defines an opening 322. Within the opening 322 is a sleeve 334. An orientation rod 324 is slidably fitted to the sleeve 334. A locking arm 328 selectively locks the sleeve 334 to the body 320. A tang 304 on the distal end of the orientation rod 324 may engage a slot 466 in the proximal end of distal stem 454 of hip stem 400. An alignment fork 310 is slidably and rotationably fitted to the body 320. The alignment fork 310 engages the sides 453 of the neck 452 of hip stem 400. When utilizing the orientation device 300 the locking arm 328 may be positioned in an unlocked position and the tang 304 angularly adjusted with respect to the alignment fork 310 until the alignment fork 310 and the tang 304 are properly seated into the proximal body 452 and the distal stem 454 of the hip stem 400, respectively.

Figure 5:
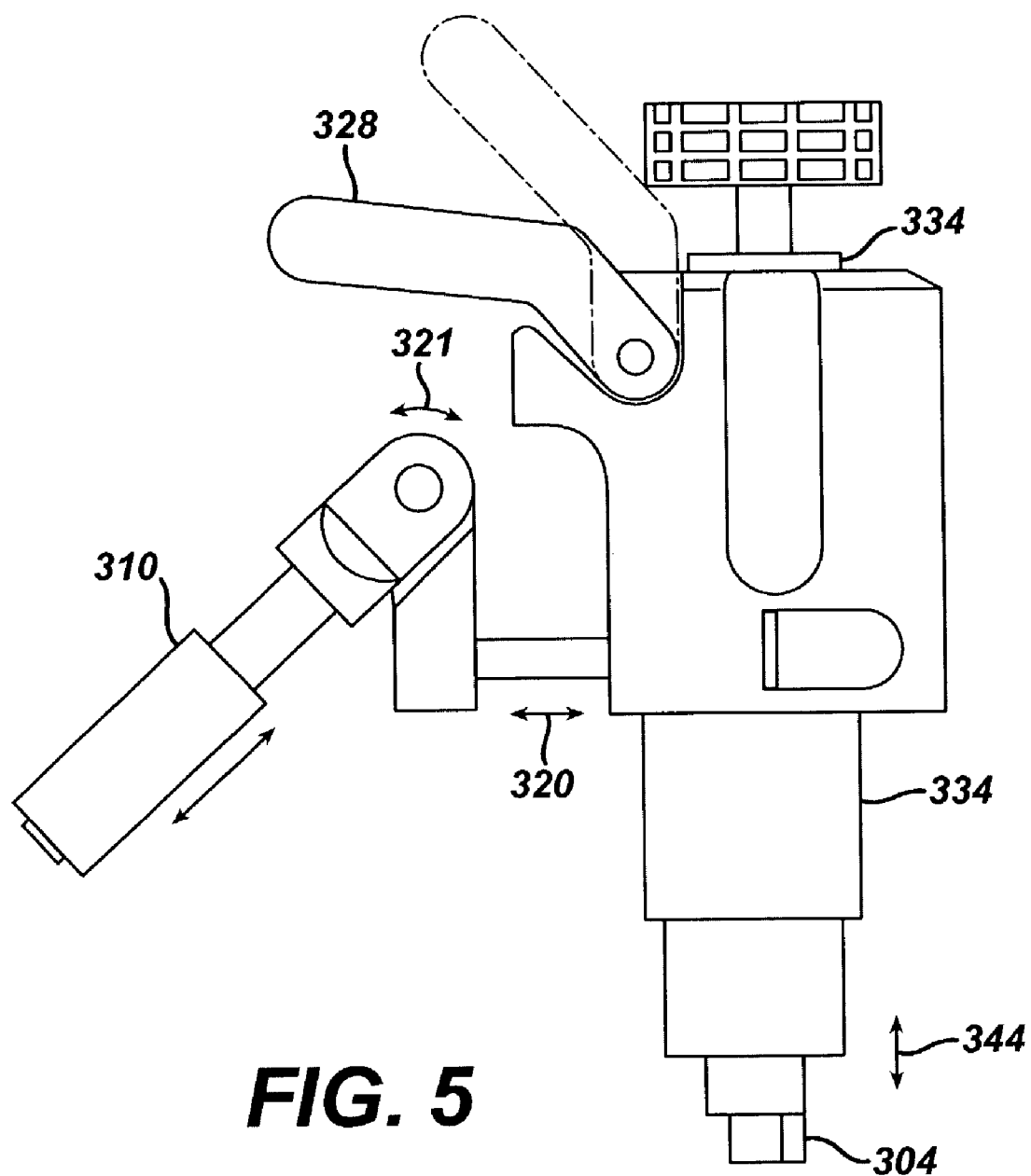
FIG. 5 is a plan view of the alignment device of FIG. 4.
Figure 6:
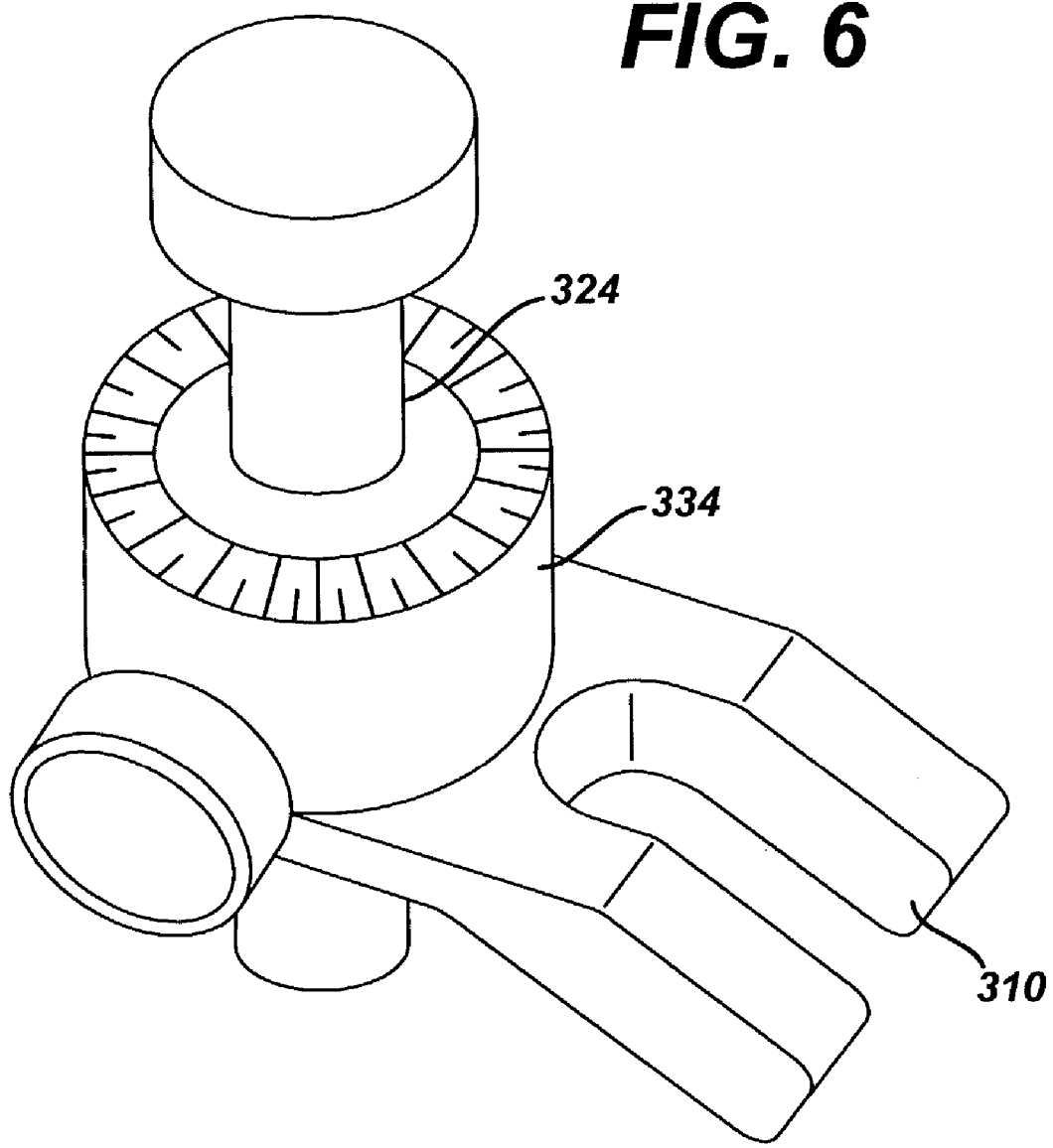
FIG. 6 is a perspective view of the fork of the alignment device of FIG. 4.

Referring now to FIGS. 5 and 6, the fork 310 is shown in greater detail. The fork 310 permits for adjustment in the directions of arrows 318, 320 and 321, providing sufficient adjustment for the fork 320 to center a number of various designs for the neck of a prosthesis. The locking arm 328 may be moved from the locked position (shown in solid) to the unlocked position (shown in phantom).

Figure 7:
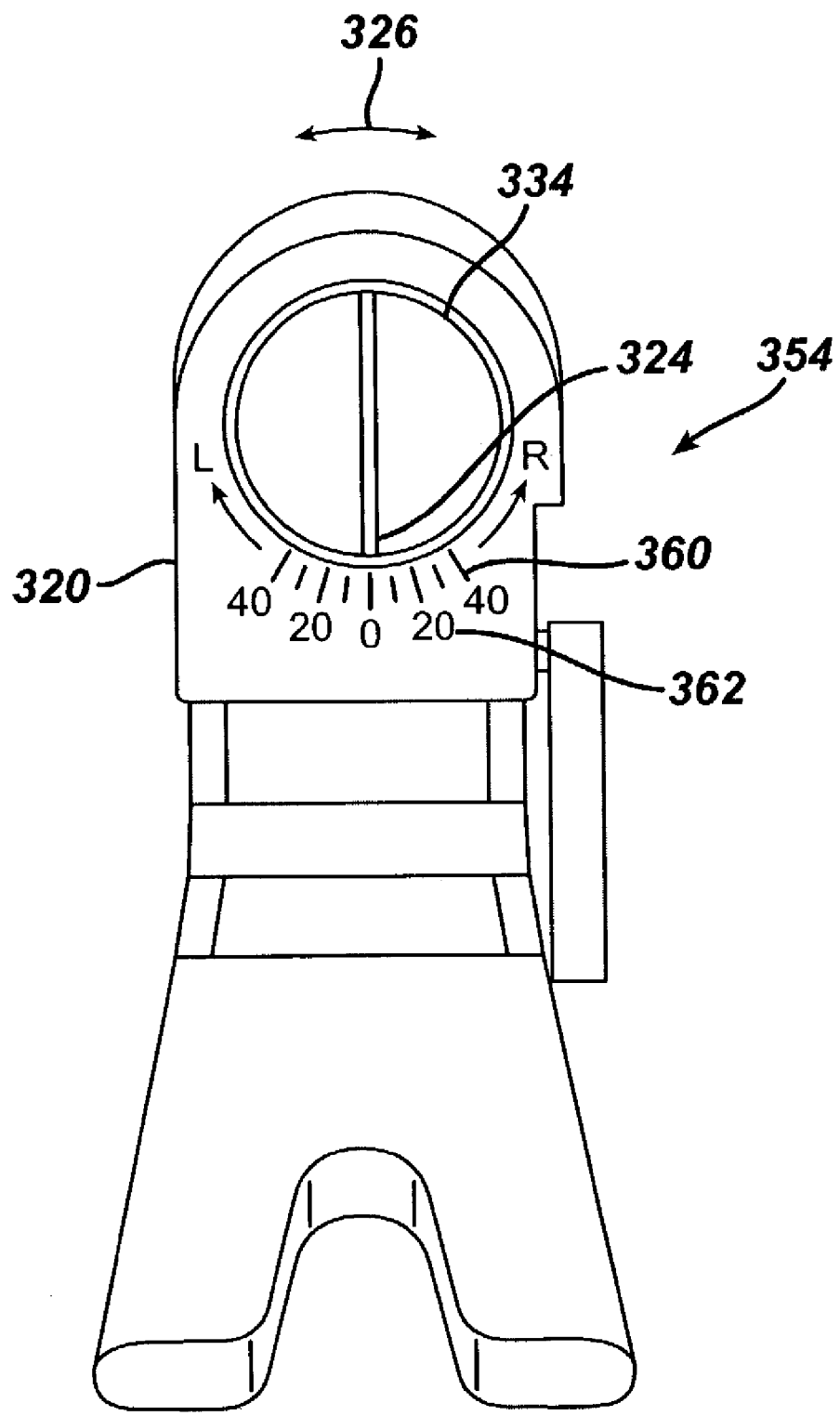
FIG. 7 is a top view of the fork of FIG. 6.
Figure 8:
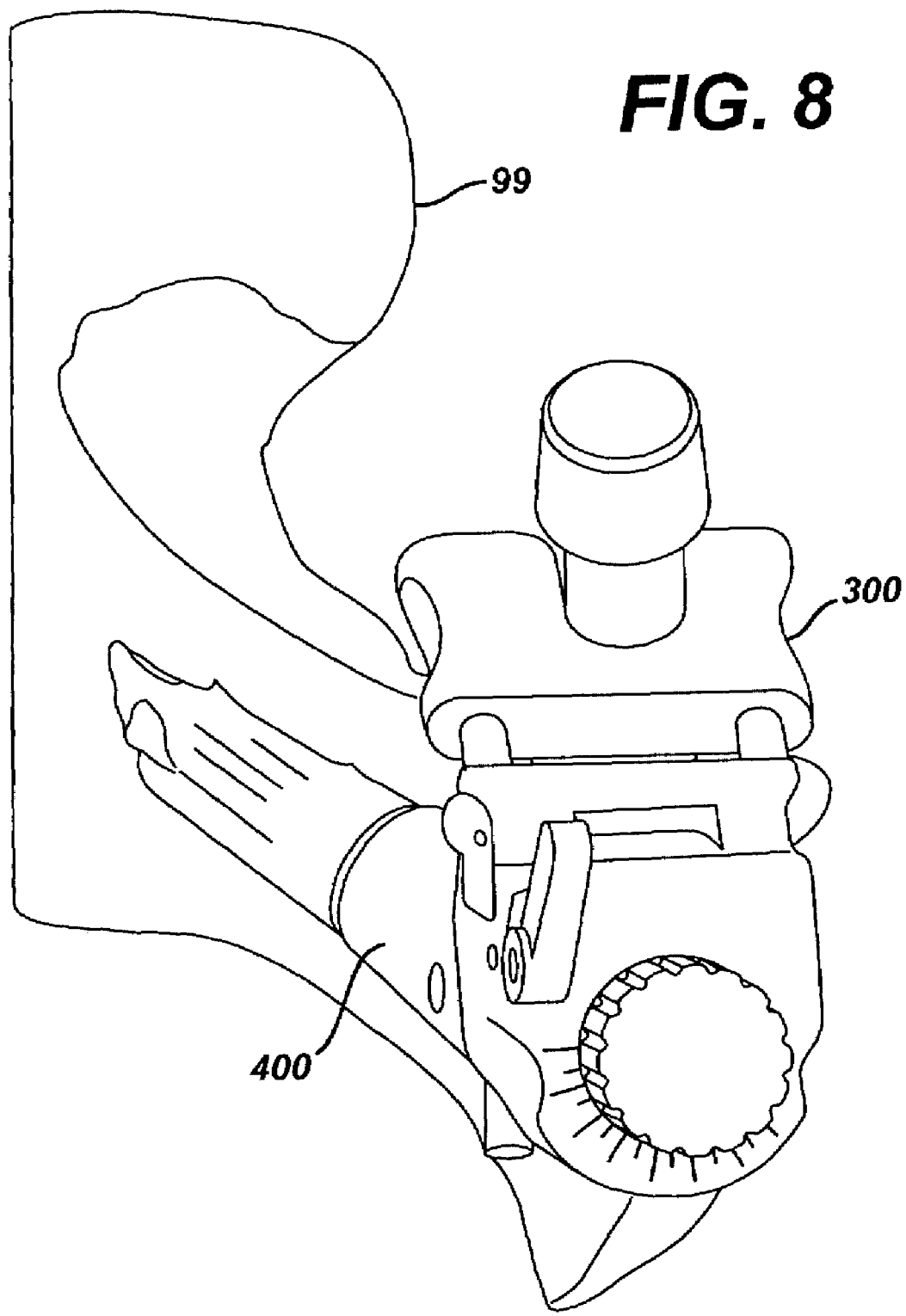
FIG. 8 is a perspective view of the alignment device of FIG. 4 shown mounted in position on a prosthesis positioned in a femur of a patient.

Referring now to FIGS. 7 and 8, the orientation device 300 may include indicia 354 similar to the indicia 254 of the orientation device 200 of FIG. 1. The indicia 354 may include a single indicia 324 located on sleeve 334 which cooperates with body indicia 360 on the body 320 to provide for a measurement of the anteversion of the hip stem 400. For example, as shown in FIG. 7, when the sleeve indicia 324 is aligned with the position 0 on the body indicia 360 of the body 320, the anteversion angle may be at the anteversion angle of zero; when the sleeve indicia 324 is aligned with the position 40 on the body indicia of the body 320, the anteversion angle may be at 40°, for example. It should be understood that these indicia are provided by way of example only, and the present invention is not limited to such indicia unless expressly called for in the claims.

Referring now to FIG. 8, the instrument 300 is shown in position on the hip stem 400 in position on hip bone 99.

Figure 26:
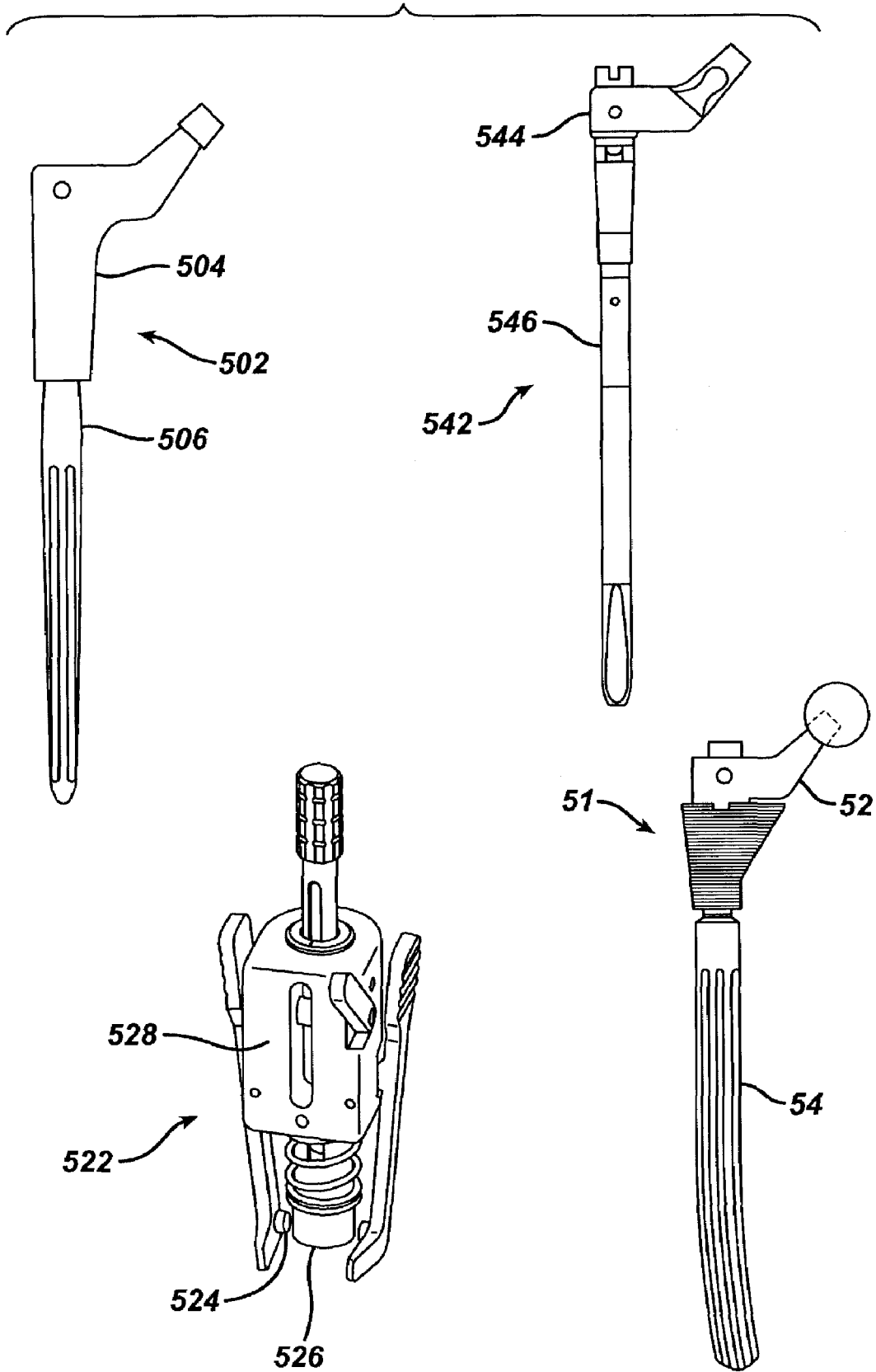
FIG. 26 is a plan view of a kit for use in arthroplasty according to the present invention.

Referring now to FIG. 26, a kit 500 according to the present invention is shown. The kit is for use in joint arthroplasty and includes a prosthesis 502 for use in joint arthroplasty. The prosthesis 502 includes a first component 504 in the form of a proximal body and a second component 506 in the form of a distal stem. The kit 500 further includes an instrument 522 for angular orientation of the first component 504 to the second component 506 of the prosthesis 502. The instrument 522 includes a first member 524 cooperation with the first component 504 and a second member 526 cooperation with the second component 506 of the prosthesis 502. The instrument 522 may further include a feature 528 in the form of a sample body for cooperating with the first member 524 and the second member 526 for observing the relative angular orientation of the first member 524 with respect to the second member 526.

The kit 500 may further include a trial 542. The trial 542 may include a first component 544 in the form of a proximal body and a second component 546 in the form of a distal stem.

Referring now to FIG. 27, a method providing arthroscopic hip arthroplasty 700 is shown. The method 700 includes a first step 702 of providing a trial prosthesis including a stem trial portion for implantation at least partially into the femoral canal of a femur and a neck trial portion extending from the stem portion. The method includes a second step 704 of positioning the stem trial portion into the femoral canal. The method includes a third step 706 of positioning the neck trial portion relative to the stem trial portion. The method 700 further includes another step 708 of securing the neck trial portion to the stem trial portion. The method further includes another step 710 of trialing the trial prosthesis.

The method 700 also includes a step 712 of attaching an instrument to the stem trial portion and the neck trial portion. The method 700 further includes step 714 of measuring the relative position of the stem trial portion to the neck trial portion. The method 700 also includes the step 716 and 718 of providing an implant prosthesis including a stem implant portion for implantation at least partially into the canal of a long bone and a neck implant portion extending from the stem portion. The method 700 also includes step 720 of positioning the stem implant into the long bone canal. The method 700 also includes the step 722 of positioning the neck implant portion relative to the stem implant portion based upon the measured relative position of the stem trial portion to the neck trial portion. The method 700 also includes the step 724 of securing the neck implant portion to the stem implant portion. The method 700 may further include the step 726 of positioning the neck implant portion relative to the stem implant portion utilizing the instrument.

Although the present invention and its advantages have been described in detail, it should be understood that various changes, substitutions, and alterations can be made therein without departing from the spirit and scope of the present invention as defined by the appended claims.

We claim:

1. An instrument for at least one of replicating and measuring the relative angular orientation of a first component of a prosthesis to a second component of the prosthesis for use in joint arthroplasty, said instrument comprising:
   a first member for cooperation with the first component;
   a second member for cooperation with the second component; and
   a feature cooperating with said first member and said second member for at least one of replicating and measuring the relative angular orientation of the first component with respect to the second component,
   wherein said first member defines a first member rotational centerline thereof, and
   wherein said second member defines a second member rotational centerline thereof, the first member rotational centerline and the second member rotational centerline are coincident with each other.

2. The instrument of claim 1, wherein said feature comprises indicia on at least one of said first member and said second member.

3. The instrument of claim 1:
   wherein said first member defines one of a recess or a protrusion thereof for engagement with the first component; and
   wherein said second member defines one of a yoke, protrusion or a recess thereof for engagement with the second component.

4. The instrument of claim 1, wherein said feature comprises:
   a plurality of first indicia on at least one of said first member and said second member; and
   a second indicia of the other of said first member and said second member.

5. The instrument of claim 1, wherein said feature comprises a body, at least one of said first member and said second member being moveably connected to said body.

6. The instrument of claim 1, further comprising a body defining an opening therethrough, a portion of said first member being rotatively positionable in the opening, said second member connected to said body.

7. The instrument of claim 6, wherein said first member is axially moveable with respect to the opening.

8. An instrument for at least one of replicating and measuring the relative angular orientation of a first component of a prosthesis to a second component of the prosthesis for use in joint arthroplasty, said instrument comprising:
   a first member for cooperation with the first component;
   a second member for cooperation with the second component; and
   a feature cooperating with said first member and said second member for at least one of replicating and measuring the relative angular orientation of the first component with respect to the second component, further comprising a lock for selectively preventing relative motion between said first member and said second member.

9. An instrument for at least one of replicating and measuring the relative angular orientation of a first component of a prosthesis to a second component of the prosthesis for use in joint arthroplasty, said instrument comprising:
   a first member for cooperation with the first component;
   a second member for cooperation with the second component; and
   a feature cooperating with said first member and said second member for at least one of replicating and measuring the relative angular orientation of the first component with respect to the second component,
   wherein said feature comprises a body, at least one of said first member and said second member being moveably connected to said body, wherein said first member, said second member and said body defining a longitudinal axis of rotation, wherein one of said first member and said second member may be rotatably keyed with said body, wherein the other of said first member and said second member is selectably rotatably movable with respect to said body, and wherein the relative angular position of said first member with respect to said second member about the longitudinal axis corresponds to the angular orientation of the first component with respect to the second component when said first member is in cooperation with the first component and when said second member is in cooperation with the second component.

10. An instrument for at least one of replicating and measuring the relative angular orientation of a first component of a prosthesis to a second component of the prosthesis for use in joint arthroplasty, said instrument comprising:
   a first member for cooperation with the first component;
   a second member for cooperation with the second component; and
   a feature cooperating with said first member and said second member for at least one of replicating and measuring the relative angular orientation of the first component with respect to the second component, wherein said feature comprises a body, at least one of said first member and said second member being moveably connected to said body, wherein said second member is pivotably connected to said body.

11. An instrument for at least one of replicating and measuring the relative angular orientation of first component of a prosthesis to a second component of a femoral stem assembly of a hip prosthesis for use in total hip arthroplasty, said instrument comprising:
   a first member for cooperation with the first component;
   a second member for cooperation with the second component; and
   a feature cooperating with said first member and said second member for at least one of replicating and measuring the relative angular position of the first member with respect to the second component,
   wherein said first member defines a first member rotational centerline thereof, and
   wherein said second member defines a second member rotational centerline thereof, the first member rotational centerline and the second member rotational centerline are coincident with each other.

12. The instrument of claim 11, wherein said feature comprises indicia on at least one of said first member and said second member.

13. The instrument of claim 11:
   wherein the first component includes a distal component;
   wherein said first member defines a protrusion thereof for engagement with the distal component;
   wherein the second component includes a neck component; and
   wherein said second member defines a yoke thereof for engagement with the neck component.

14. The instrument of claim 11, wherein said feature comprises:
   a plurality of first indicia on at least one of said first member and said second member; and
   a second indicia of the other of said first member and said second member.

15. The instrument of claim 11, further comprising a body defining an opening therethrough, a portion of said first member being rotatively positionable in the opening, said second member connected to said body.

16. The instrument of claim 15, wherein said first member is axially moveable with respect to the opening.

17. An instrument for at least one of replicating and measuring the relative angular orientation of first component of a prosthesis to a second component of a femoral stem assembly of a hip prosthesis for use in total hip arthroplasty, said instrument comprising:
   a first member for cooperation with the first component;
   a second member for cooperation with the second component; and
   a feature cooperating with said first member and said second member for at least one of replicating and measuring the relative angular position of the first member with respect to the second component, further comprising a lock for selectively preventing relative motion between said first member and said second member.

18. An instrument for at least one of replicating and measuring the relative angular orientation of first component of a prosthesis to a second component of a femoral stem assembly of a hip prosthesis for use in total hip arthroplasty, said instrument comprising:
   a first member for cooperation with the first component;
   a second member for cooperation with the second component; and
   a feature cooperating with said first member and said second member for at least one of replicating and measuring the relative angular position of the first member with respect to the second component, further comprising a body defining an opening therethrough, a portion of said first member being rotatively positionable in the opening, said second member connected to said body, wherein said second member is pivotably connected to said body.

* * * * *